United States Patent
Richardson et al.

[11] Patent Number: 5,976,083
[45] Date of Patent: Nov. 2, 1999

[54] PORTABLE AEROBIC FITNESS MONITOR FOR WALKING AND RUNNING

[75] Inventors: J. Jeffrey Richardson, Boulder; Ted D. Wade, Littleton, both of Colo.

[73] Assignee: Living Systems, Inc., Boulder, Colo.

[21] Appl. No.: 08/902,748

[22] Filed: Jul. 30, 1997

[51] Int. Cl.⁶ ........................................ A61B 5/02

[52] U.S. Cl. .................. 600/300; 600/481; 600/587; 482/8; 482/901

[58] Field of Search ..................... 600/500, 502, 600/520, 587, 592, 595; 482/3, 4, 8, 9, 900, 901, 300, 481

[56] References Cited

U.S. PATENT DOCUMENTS

| | | | |
|---|---|---|---|
| 4,192,000 | 3/1980 | Lipsey | 482/8 |
| 4,434,801 | 3/1984 | Jiminez et al. | 600/502 |
| 4,566,461 | 1/1986 | Lubell et al. | 600/481 |
| 4,757,453 | 7/1988 | Nasiff | 364/415 |
| 4,771,394 | 9/1988 | Cavanagh | 364/561 |
| 4,830,021 | 5/1989 | Thornton | 600/520 |
| 4,867,442 | 9/1989 | Matthews | 482/8 |
| 5,117,444 | 5/1992 | Sutton et al. | 377/24.2 |
| 5,314,389 | 5/1994 | Dotan | 482/3 |
| 5,435,315 | 7/1995 | McPhee et al. | 600/502 |
| 5,485,402 | 1/1996 | Smith et al. | 364/566 |
| 5,524,637 | 6/1996 | Erickson | 600/592 |

*Primary Examiner*—Cary O'Connor
*Assistant Examiner*—Charles Marmer, II
*Attorney, Agent, or Firm*—Jay R Beyer; Stephen C Sheer

[57] ABSTRACT

A personal fitness monitoring device and a method for assessing the fitness of an individual as the individual exercises includes using a pedometer to determine and output data representing the locomotion of the individual. A heart rate monitor determines and outputs data representing the heart rate of the individual. A determination arrangement calculates the fitness of the individual as the individual exercises using personal data provided by the individual in combination with the data outputs of the pedometer and the heart rate without requiring a predetermined exercise regime. In one embodiment, the pedometer calculates a distance traveled by the individual using personal data provided by the individual. The personal fitness monitoring device may further include a user interface for communicating with the user. The user interface uses a single user controlled selecting mechanism to select a desired one of various user selectable options. The single user controlled selecting mechanism is arranged such that the user selects the desired option by actuating the selecting mechanism during or immediately following the time during which the desired option is being presented by the user interface. The personal fitness monitoring device may also include a predicting arrangement for tracking and predicting the fitness of the individual.

23 Claims, 14 Drawing Sheets

PORTABLE AEROBIC FITNESS MONITOR FOR WALKING AND RUNNING

BACKGROUND OF THE INVENTION

The present invention relates to personal fitness monitoring devices. More specifically, the invention relates to a personal fitness monitoring device that may be worn by an individual while the individual is exercising. The fitness monitoring device monitors the aerobic fitness of the user as the user exercises and provides the user with information about the current exercise session, an assessment of the user's current fitness level, and a prediction of the user's future fitness.

SUMMARY OF THE INVENTION

A personal fitness monitoring device and a method for assessing the fitness of an individual as the individual exercises is herein disclosed. The fitness monitoring device includes a pedometer for determining and outputting data representing the locomotion of the individual. A heart rate monitor determines and outputs data representing the heart rate of the individual. A determination arrangement calculates the fitness of the individual as the individual exercises using personal data provided by the individual in combination with the data outputs of the pedometer and the heart rate monitor without requiring a predetermined exercise regime.

In one embodiment, the pedometer of the personal fitness monitoring device includes an accelerometer for measuring and outputting data representing the vertical accelerations caused by each step of the individual as the individual is walking or running. A clock is used to segment the output of the accelerometer into a time series of data points representing the output of the accelerometer. A distance determination arrangement calculates a distance traveled by the individual using personal data provided by the individual in combination with the data outputs of the accelerometer and the clock.

In another embodiment, the personal fitness monitoring device further includes a user interface for communicating with the user. The user interface includes menus having a plurality of various user selectable options available to the user for controlling the operation of the personal fitness monitoring device. The various user selectable options of the menus are successively presented to the user. A single user controlled selecting mechanism is used for selecting a desired one of the various user selectable options of the menus. The single user controlled selecting mechanism is arranged such that the user selects the desired option by actuating the selecting mechanism during or immediately following the time during which the desired option is being presented by the user interface.

In one version of the above described embodiment, the arrangement for presenting the various user selectable options to the user is provided by an audio producing arrangement which presents the options to the user in the form of recorded or synthesized speech. This embodiment may further include an auxiliary audio fader arrangement. The audio fader arrangement has an auxiliary audio input connector for receiving an auxiliary audio input signal from an auxiliary audio device. A fader, which is controlled by the operation of the personal fitness monitoring device, connects the auxiliary audio input signal to an audio output device used by the user interface of the personal fitness monitoring device to present the user interface messages. The fader is configured to suppress the auxiliary audio input signal when the user interface of personal fitness monitoring device presents a message to the user.

In another embodiment, the personal fitness monitoring device further includes a predicting arrangement for tracking and predicting the fitness of the individual. The predicting arrangement includes a memory arrangement for storing the data representing the fitness of the individual each time the individual exercises using the personal fitness monitoring device. A fitness projecting arrangement calculates a projected fitness of the individual. The fitness projecting arrangement uses the stored data representing the fitness of the individual each time the individual exercises using the personal fitness monitoring device to calculate the projected fitness of the individual.

In another aspect of the invention, a pedometer and a method for calculating the distance traveled by an individual as the individual walks or runs is herein disclosed. The pedometer includes an accelerometer for measuring and outputting data representing the vertical accelerations of each step of an individual as the individual is walking or running. A clock is used to segment the output of the accelerometer into a time series of data points representing the output of the accelerometer. The pedometer also includes a determination arrangement for calculating a distance traveled by the individual. The determination arrangement uses personal data provided by the individual in combination with the data outputs of the accelerometer and the clock to calculate the distance traveled.

In another aspect of the invention, a user interface for use in a personal fitness monitoring device and a user interface method are herein disclosed. The user interface includes menus having a plurality of various user selectable options available to the user for controlling the operation of the personal fitness monitoring device. An audio producing arrangement is used to present the various user selectable options of the menus to the user in the form of recorded or synthesized speech. A single user controlled selecting mechanism is used to select a desired one of the various user selectable options of the menus. The single user controlled selecting mechanism is arranged such that the user selects the desired option by actuating the selecting mechanism during or immediately following the time during which the desired option is being presented in the form of recorded or synthesized speech.

In another aspect of the invention, an auxiliary audio fader arrangement and method for use in a personal fitness monitoring device which includes an audio user interface for presenting user interface audio messages to a user in order to interface with the user is herein disclosed. An auxiliary audio input connector receives an auxiliary audio input signal from an auxiliary audio device. A fader, which is controlled by the operation of the personal fitness monitoring device, connects the auxiliary audio input signal to an audio output device used by the audio user interface of the personal fitness monitoring device to present the user interface audio messages. The fader is configured to suppress the auxiliary audio input signal when the audio user interface of personal fitness monitoring device presents an audio message to the user.

And finally, in another aspect of the invention, a personal fitness monitoring device and method for tracking and predicting the fitness of an individual is herein disclosed. The fitness device includes an exertion determining arrangement for determining and outputting data representing the exertion of the individual as the individual is exercising. A heart rate monitor is used to determine and output data representing the heart rate of the individual. A fitness determination arrangement calculates and outputs data representing the fitness of the individual as the individual exercises.

The determination arrangement uses personal data provided by the individual in combination with the data outputs of the exertion determining arrangement and the heart rate monitor to calculate the fitness of the individual. A memory arrangement stores the data representing the fitness of the individual each time the individual exercises using the personal fitness monitoring device. A fitness projecting arrangement calculates a projected fitness of the individual. The fitness projecting arrangement uses the stored data representing the fitness of the individual each time the individual exercises using the personal fitness monitoring device to calculate the projected fitness of the individual.

BRIEF DESCRIPTION OF THE DRAWINGS

The features of the present invention may best be understood by reference to the following description of the presently preferred embodiments together with the accompanying drawings in which.

DETAILED DESCRIPTION

Figure 1:
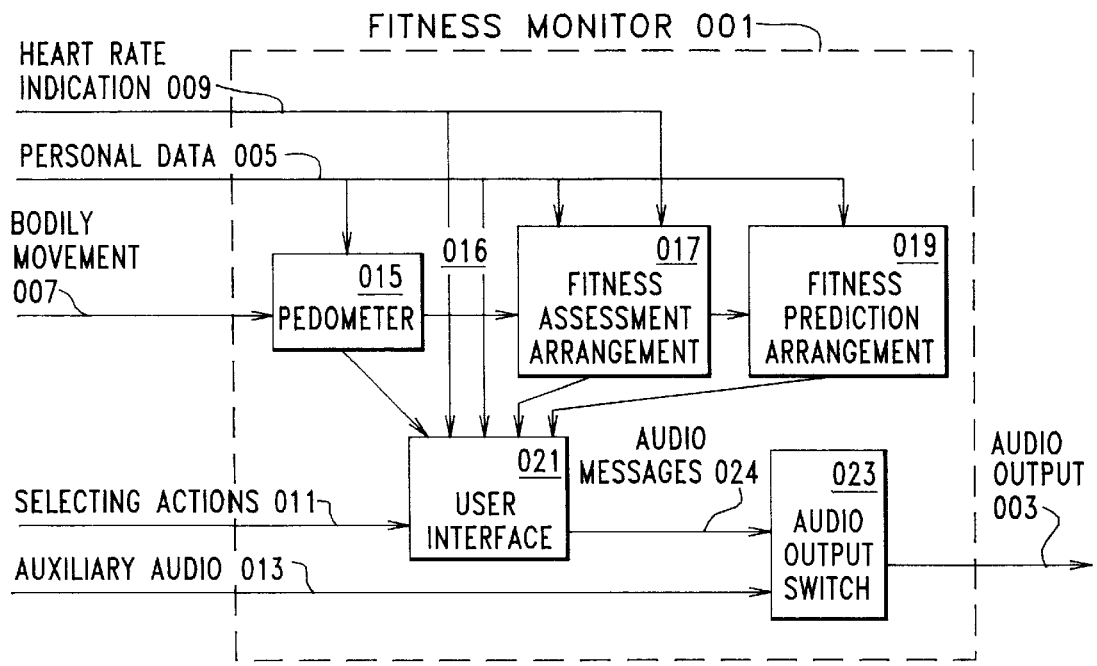
FIG. 1 is a diagrammatic illustration of one embodiment of a personal fitness monitor in accordance with the present invention.

FIG. 1 shows an embodiment of a fitness monitor 001, designed in accordance with the invention. When worn on the human body while exercising on multiple occasions over the course of many days, fitness monitor 001 provides the user, as its primary output, an audio output 003. Audio output 003 may take the form of synthesized or digitized voice messages detailing the user's current exercise session, an assessment of the user's current level of fitness, and a prediction of the user's future fitness.

Fitness monitor 001 takes as primary input certain user's personal data 005, an indication of the user's bodily movement 007, an indication of the user's heart rate 009, any user selecting actions 011, and an auxiliary audio input 013, all of which will be described hereinafter. Fitness monitor 001 has as constituent components a pedometer 015, a fitness assessment arrangement 017, a fitness prediction arrangement 019, a user interface 021, and an audio output switch 023, all of which will also be discussed hereinafter.

Taking as inputs bodily movement 007 and personal data 005, pedometer 015 produces a locomotion parameters signal 016 representing the users walking or running locomotion. Signal 016 indicates locomotion parameters associated with each step that the user takes during an exercise session. The locomotion parameters include the gait, duration, speed, and distance of each step, and optionally, grade and terrain characteristics.

The output signal 016 of pedometer 015 is taken as input to fitness assessment arrangement 017 which also takes as input heart rate indication 009 and personal data 005. The fitness assessment arrangement 017 then computes an estimate of the user's current fitness, a measure of the aerobic capacity of the user. This output may be expressed in one of several common units of measure, including ml oxygen per minute and kilogram body weight, known as $VO_2$, metabolic equivalents, known as METs, or any commonly used measure of indication of fitness, including qualitative measures such as "good" or "poor."

The output of fitness assessment arrangement 017 is input to fitness prediction arrangement 019, which also takes as input personal data 005. The fitness prediction arrangement 019 produces as output a signal that represents the rate of change and future trajectory of the user's aerobic fitness. This output is reported on demand to the user through suitable means according to the particular embodiment of the invention, for example as a text display or as pre-recorded or synthesized speech. However, the format of the output is not a requirement of the invention and it may vary considerably.

The fitness monitor 001 also includes a user interaction arrangement, user interface 021. User interface 021 provides a means for the user to communicate with fitness monitor 001 by coordinating the timing of a selecting action 011 with the temporal period during which a choice is presented. User interface 021 provides as an output certain audio messages 024.

Finally, fitness monitor 001 includes audio output switch 023 which takes as input both audio messages 024 of fitness monitor 001 and auxiliary audio 013 the user may wish to hear. The purpose of the audio output switch 023 is to permit users to attend to their desired auxiliary programming yet to also permit this programming to be interrupted or faded out in order that users can hear important messages initiated by fitness monitor 001. For example, users will be able to listen to a portable tape recorder or radio and to fitness monitor 001 through the same set of earphones as will be described hereinafter.

While fitness monitor 001 is described as being composed of pedometer 015, fitness assessment arrangement 017, fitness prediction arrangement 019, user interface 021, audio output switch 023, and inputs representing bodily movement 007, personal data 005, heart rate indication 009, selecting actions 011, and auxiliary audio 013, the presence of all of these components is not essential to this invention, and the existence of certain additional components would be consistent with the invention. For example, a non-audio version of fitness monitor 001 could be constructed without the requirement of audio output switch 023.

A version of fitness monitor 001 comprised of any of its components alone would be a useful device, for example, pedometer 015 alone, or fitness prediction arrangement 019 alone. Or several constituents could be present, while others are absent, for example, pedometer 015, fitness assessment arrangement 017, and fitness prediction arrangement 019 would provide a useful fitness monitoring device employing some means of user interaction other than user interface 021 as described herein. Similarly, pedometer 015 is not a requirement of the invention because other methods of detecting and reporting distance traveled, speed of traveling, or expended energy in general might be employed, such as global positioning systems or Doppler sound ranging techniques. In a like manner, fitness prediction arrangement 019 is not a requirement of the invention because the fitness monitoring function can be fully realized by computing and reporting the user's current fitness without regard to or need to predict the future trends in fitness.

In summary, the constituent components of this invention can be assembled into numerous configurations by including some components and leaving others out. All such useful combinations would be consistent with the invention. On the other hand, the invention may be augmented with additional components without changing the nature of this invention.

For example, the invention could include in its functioning access to sources of auditory programming, such as recorded audio, broadcasts, or digital text that could be translated to voice for presentation to the user. That is, the invention could include a component designed to provide the user with pager messages, email messages, and Internet information bulletins. Audio messages could also be used for encouragement, advice, and inspiration. A remote clinic's computer could send fitness goals and a suggested exercise regimen to the fitness monitor 001, which could in turn report back on compliance with the regimen and fitness changes for review by clinic personnel.

As another example of additional components, the fitness monitor 001, when combined with a personal digital assistant scheduling program, could arrange times for the user to exercise. A home scale could supply body weight, which is needed by the fitness monitor 001 for many of its calculations. A kitchen appliance used for recipes, diet and menu planning could give an estimate of dietary fat, which the fitness monitor 001 could use in recommending fitness goals, and explaining fitness progress. The fitness monitor 001 in turn could supply fitness and body weight to the dietary computer, which could use them to make dietary recommendations.

While several examples have been cited of additional components to which the invention might be connected, these examples are only indicative of the range of inputs to and outputs from the invention described herein. Customized inputs for these components could be readily provided and/or user interface 021 could be designed to accommodate all of these components through one or more auxiliary inputs.

The principal advantage of the invention consistent with the embodiment as fitness monitor 001 is that previous approaches have provided no equivalent function of calculating fitness while the user is engaged in normal exercise activity and without the requirement that the user follow a specific testing protocol conducted in a specific location in order to determine fitness. A further advantage is that, due to the ease of calculating fitness, it is possible to obtain a time series of fitness data points across a number days which permits a trend in fitness to be computed and reported to the user.

Pedometer 015

Although pedometer 015 has been described as being included in fitness monitor 001, this is not a requirement of the invention. Instead, pedometer 015 may be used alone while walking or running to provide information about locomotor activity, including gait, total distance traveled, calories consumed, current and average speed of travel, and current grade of the terrain.

Figure 2:
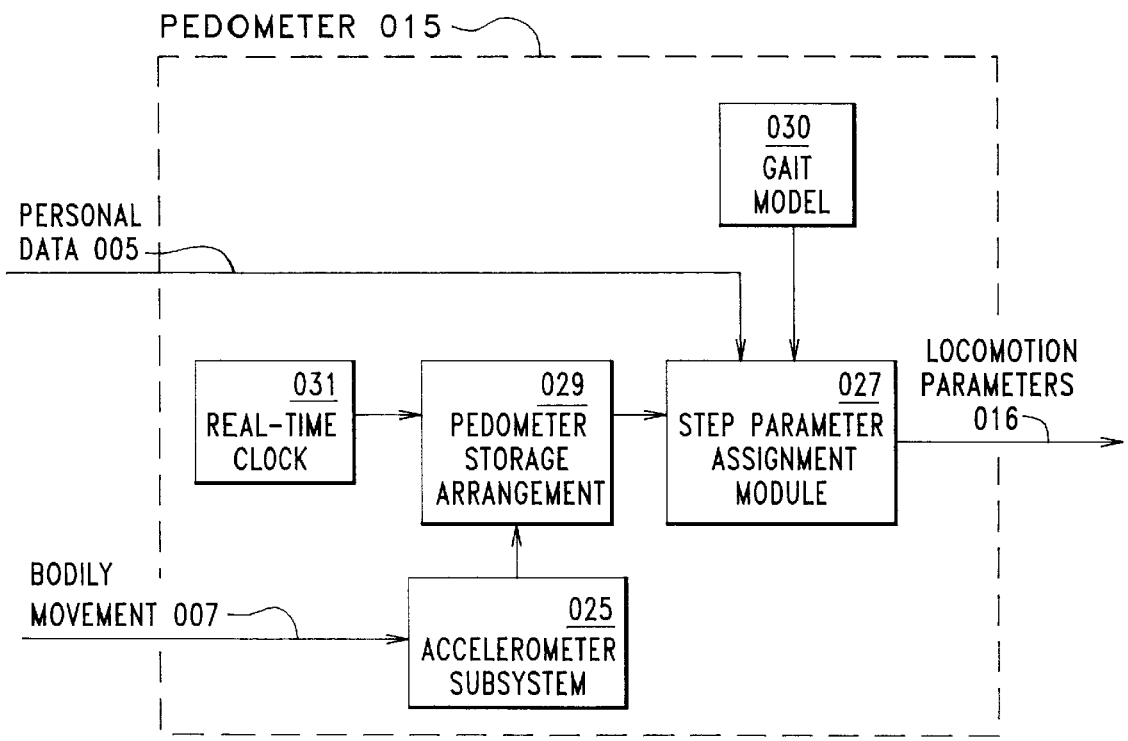
FIG. 2 is a diagrammatic illustration of one embodiment of a pedometer in accordance with the present invention.

FIG. 2 shows an embodiment of pedometer 015 designed in accordance with the invention. Pedometer 015 includes an accelerometer subsystem 025, a step parameter assignment module 027, a pedometer storage arrangement 029, and a real-time clock 031. Pedometer 015 takes as input personal data 005 and bodily movement 007 and provides as output locomotion parameters 016. Accelerometer subsystem 025 measures the on-going instantaneous profile of the user's movement as magnitudes of acceleration in or near the vertical plane and stores these magnitudes in pedometer storage arrangement 029 as a time series wherein each instantaneous moment's acceleration is associated with a time provided by the real-time clock 031. A more detailed discussion of the way in which pedometer 015 operates will be provided hereinafter in conjunction with FIGS. 13 and 14.

Step parameter assignment module 027 makes use of the varying magnitude of acceleration in the vertical or near-vertical plane as an individual walks or runs as recorded in pedometer storage arrangement 029. Prior art pedometers base the measurement of distance on ascribing (a) a predetermined length to each step, (b) a variable length based only on the stride time, (c) or, one of several alternative predetermined lengths associated with one of several predetermined gaits. The present invention bases the measurement of distance covered by a series of steps by assigning a certain distance and speed to each step depending on the characteristics of the near-vertical acceleration waveform produced by that step.

It is not a requirement of this invention that the vertical or near-vertical acceleration magnitude be associated with any one temporal instant during the course of a step. For example, the magnitude employed by step parameter assignment module 027 might be associated with the heel strike, or the toe push-off. Given embodiments of the invention could require that step parameter assignment module 027 employs acceleration magnitudes from multiple or even all temporal instants during the course of a step. A step begins with a left (or right) foot heel strike and continues through and ends with the right (or left) foot heel strike.

The step parameter assignment module 027 employs personal data 005 in ascribing the correct gait and speed to associate with a step. Step parameter assignment module 027 employs a network of decisions, implemented as gait model 030. Gait model 030 assigns to a given vertical or near vertical acceleration magnitude or profile an associated gait and speed of locomotion. This assignment is dependent on the characteristics of the user, such as height, leg length, gender, age, or weight, as represented by personal data 005. That is, personal data 005, taken together with the output of acceleration subsystem 025 provides a powerful and reliable estimate of locomotor gait and speed of each step.

Described in detail hereinafter in conjunction with FIG. 14 and Table 3, gait model 030 subjects the vertical or near vertical acceleration magnitude associated with a given step to a series of yes/no classification decisions dealing with the magnitude of the acceleration and the user's personal data 005. The resulting classification associates with each step a certain gait and speed. Gait takes on one of two values, either "walking" or "running", unless the user is not locomoting. In the latter case, the gait model takes the value of "rest".

Gait model 030 is a statistical compendium of numerous users, wherein users' walking or running acceleration profiles and personal characteristics were used to predict the speed of each step for a given user. The resultant gait model 030 has general validity in that it may be applied to persons not involved in deriving the model. Thus, through the means of gait model 030 and personal data 005, pedometer 015 has an automated mechanism within it to adjust to the characteristics of a given user.

Gait model 030, while presented here in pedometer's 015 main embodiment, is not a requirement of the invention. For example, it would be possible to ask the user to execute a calibration protocol which would generate a gait model 030 based on and useful solely for that particular individual.

As described above, personal data 005 include user gender, age, weight, height, and leg length. However, it is not a requirement of the invention that all of these quantities are present or used, for example, leg length may not be a requirement. Similarly, it is not a requirement of the invention that only these quantities are used. For example, arm length, chest size, or other measurements of qualities of the user as an individual may be incorporated by step parameter assignment module 027 to make as accurate as possible a determination of a given step's gait, distance or speed.

Real-time clock 031 is used in the preferred embodiment of pedometer 015 for three purposes. First, it is used to segment the output of the accelerometer into a time series of data points representing the output of the accelerometer. That is, the clock is used to ascribe a timing to each measurement of magnitude of acceleration made by accelerometer subsystem 025. Each of the resulting time-and-acceleration pairs of numbers is in turn used by step parameter assignment module 027. Second, real-time clock 031 is used to translate the speeds of successive steps into a distance traveled. This is done by employing the relationship of distance equals speed times duration. Third, real-time clock 031 is used to measure the elapsed time of an exercise session.

The use of real-time clock 031 for each of these purposes is not a requirement of the invention. For example, it is not required that pedometer 015 report elapsed time. Further, it would be consistent with the invention for the step parameter assignment module 027 to provide a signal representing distance traveled rather than speed, avoiding the need to use real-time clock 031 in a distance equals speed times duration calculation.

Although pedometer 015 has been described as calculating the step-wise gait and distance or speed traveled by an individual, it may also calculate other quantities based on its configuration. For example, pedometer 015 may calculate a smoothed average speed over a recent interval of time, or parameters descriptive of the terrain and environment of locomotion, such as the current grade or slope, or the nature of the surface, such as hard pavement, gravel, turf, or sand. Pedometer 015 may also calculate and output measures of energy expenditure, such as calories consumed. These additional parameters may be outputted by pedometer 015 as locomotion parameters 016 along with speed or distance.

The grade and terrain associated with a given step is determined from the time series profile of the vertical or near vertical accelerations associated with a step. As hereinafter described in greater detail in conjunction with FIG. 13, a step's profile has a double peak associated with each heel strike and toe push-off. The relative heights of these peaks and their temporal spacing within a given step's acceleration profile vary with the grade of the locomotor substrate.

Gait is not limited to walking and running, but may include other more subtle gradations of gait, such as "shuffling" or "sprinting", as well as qualities of gait, such as left-right asymmetry or degrees of skeletal shock absorption.

The advantage of pedometer 015 is that it is more accurate than pedometers that measure distance by counting steps or other movements and ascribing a fixed distance to each. It is well known that stride length varies continuously with speed. Thus, any attempt to measure distance by counting steps is inherently inaccurate. Another advantage of pedometer 015 is that it does not require calibration. Calibration is avoided by the presence of gait model 030 which adjusts pedometer 015 to the current user based on personal data 005. Thus, the user is not inconvenienced by having to go through a special calibration routine beyond the entering of personal data 005. A fourth advantage of pedometer 015 is that, through the detection of acceleration magnitude profiles by accelerometer subsystem 025, it would be possible to provide data useful for gait analysis, such as whether foot impacts on the ground are more intense than necessary, or if one foot is impacting harder than the other.

User Interface 021

Although we have described user interface 021 as being included in the overall fitness monitor 001, this is not a requirement of the invention. Instead, the user interface 021 may be used independently and separately from the fitness monitor 001 as the controlling mechanism of another device.

It is common for there to be a plurality of controls, such as knobs, buttons, or keys, associated with a device that has a plurality of functions to be controlled, in an arrangement where one control is associated with each function. For example, a radio might have two knobs, one for volume and one for tuning. As another example, a voice messaging service might use many of the different numbered keys on the telephone keypad to indicate different commands. Often, this plurality of controls becomes an obstacle to ease of use, there being too many knobs and buttons to remember or find which one does what. It is the object of user interface 021 to simplify the interaction between device and user to one single control whose function is determined by the current context of interaction.

Figure 3:
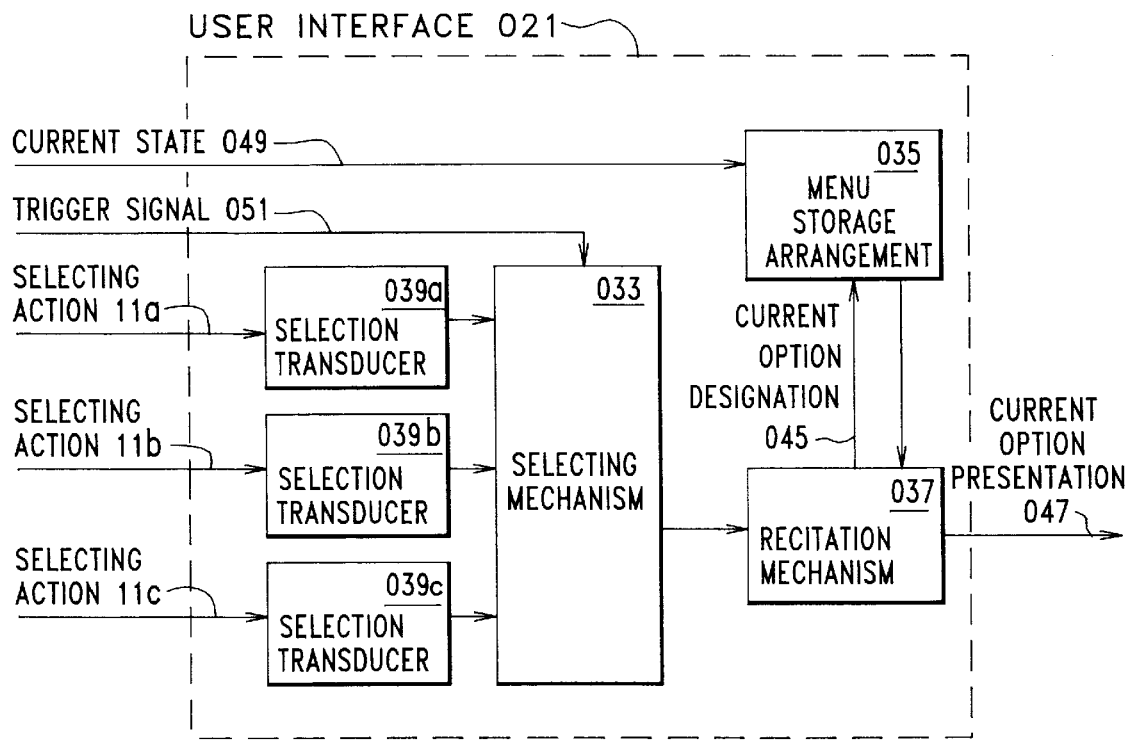
FIG. 3 is a diagrammatic illustration of a user interface in accordance with the present invention.

FIG. 3 illustrates one embodiment of a user interface designed in accordance with the invention and designated by reference numeral 021. User interface 021 includes a selecting mechanism 033, a menu storage arrangement 035, a recitation mechanism 037, and one or more selection transducers 039a, 039b, and 039c. Selection transducers 039a, 039b, or 039c are used to detect an input signal in the form of selecting actions 011a, 011b, or 011c. Upon recognition of a selecting action 011, the selection transducers 039a, 039b, or 039c provide a signal indicating the presence of the selection actions to the selecting mechanism 033. The selecting mechanism 033 indicates as its output either the presence or absence of a user selecting action 011 by logically ORing or otherwise logically combining the inputs from the selection transducers 039a, 039b, or 039c. For example, in the preferred embodiment, the selection action 011 is pressing a single large control button on the face of fitness monitor 001. This control button serves as the selection transducer 039. When it is pressed, a signal is sent to the selection mechanism 033 indicating the user has interacted with fitness monitor 001.

Upon the indication of a selecting action 011 by selecting mechanism 033, recitation mechanism 037 will begin presenting in temporal sequence a series of menu options, the options being provided by menu storage arrangement 035. Which menu in 035 to retrieve is conditioned by a current option designation 045 output from recitation mechanism 037. This output reflects which menu and menu element is active when the selecting mechanism 033 issues its output, that is, it indicates which option the user picks.

The following example, which is hereinafter presented in further detail in conjunction with FIG. 16, will be used to illustrate the functioning of user interface 021. In this example, user interface 021 utilizes one single selection transducer 039, in this case a single control button. Suppose the user interface 021 is about to begin presentation of a More Choices menu. First, the elements of this menu are retrieved from menu storage arrangement 035 and several utterances are queued up in recitation mechanism 037 for recital, namely: "Reports?," "Alarms?," "Personal data?," and "Your preferences?" These utterances are then recited, one after another. If recitation mechanism 037 receives no input from selection mechanism 033 that the user has picked an item by the time the item's utterance is completed, then recitation mechanism 037 goes on to the next item.

In the example described above, the utterances "Reports?" and "Alarms" are presented in succession and output to the user by a current option presentation signal 047as speech. However, suppose that upon hearing "Personal data?" and before hearing the next item, the user presses the control button. This selecting action 011, that is the pressing of the control button, causes the selection transducer 039, a normally open switch underneath the control button, to send a signal to the selecting mechanism 033. Since that signal is received while the utterance, "Personal data?" is being recited, this causes the current option designation 045 to indicate back to the menu storage arrangement 035 that the menu item "Personal data?" has been selected. This alters the state of menu storage arrangement 035 such that it now issues a subsequent menu to the recitation mechanism 037 for recital that involves the choices pertaining to setting personal data 005.

The content of the menus to be recited is also affected by a current state signal 049. For example, in the case of personal data 005, the personal data items for the user are presented with each personal data item including a value (e. g. "Age is 45 years"). It is the current state signal 049 input to the menu storage arrangement 035 that supplies this value.

Selecting mechanism 033 may be triggered by events not involving the user's selecting action 011. For example, the selecting mechanism may be triggered by conditions pertinent to a device's internal operation or external environment. A trigger signal 051 is the input that accomplishes this. For example, if the user has just completed an increment of distance called a milestone, trigger signal 051 would be activated causing recitation mechanism 037 to retrieve and recite a Milepost Alarm as will be described in more detail hereinafter with regard to Table 1. The values presented in that menu, as described above, are provided by context signal 049.

Current option presentation signal 047 may be presented in any of a number of modalities, including but not limited to an audio output 003 of recorded or synthesized speech as described above. Alternatively, an LCD display or other conventional output device could be employed instead.

The selection transducer 039 of the above example was described as a having a single channel of input, that is, the single control button. This is not a requirement of the invention. Instead, there may be a second selecting action 011 to which selecting mechanism 033 will respond, or even a plurality of selecting actions 011, (shown in FIG. 3 as 11a, 11b, and 11c).

Accordingly, the selection mechanism 033 may receive input signals from any number of selection transducers, represented in FIG. 3 as 039a, 039b, and 039c. These correspond to different modalities of selecting action 011 for the user to employ. For example, selection transducer 039a might be a control button as previously described. Selection transducer 039b might be a detector of vocal utterance such as a "grunt" which would be used to produce a signal in the same manner as a button press. And finally, selection transducer 039c might be a detector of brainwave patterns, a burst of electromagnetic activity associated with thinking "pick this one." However, even in the case where selecting mechanism 033 takes input from three distinct selection transducers 039a, 039b, and 039c, the presence of a signal triggering any one of these three receptors, that is, a button press, a verbal sound, or a certain brainwave pattern, are all equivalent and cause selecting mechanism 033 to indicate a selection has been made. That is, the selection action channels are ORed by the selecting mechanism 033.

The principal advantage of the user interface 021 is that it provides a way for controlling devices having a plurality of functions through the use of only one control, for example, a single knob, button, or key. The benefit of this advantage is in its simplicity of manipulation for the user, a benefit especially apparent for devices that need to be operated in the dark, in poor lighting, or while the user is otherwise moving, such as while using fitness monitor 001. The use of voice in the described embodiment provides the advantage that devices can be operated more safely because the user's eyes are freed for other uses associated with operating the device at hand. A final advantage is that, compared to common voice menu systems, such as are used in automated voice response systems, user interface 021 eliminates the need for remembering numbered options and pressing the different buttons for each of those options.

Audio Output Switch 023

Figure 4:
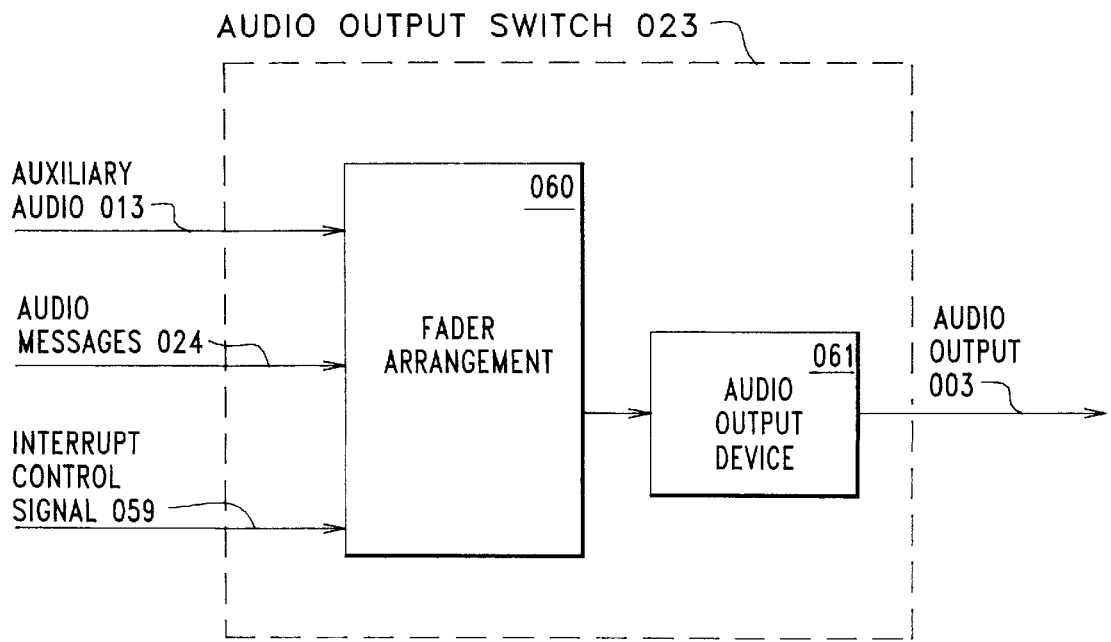
FIG. 4 is a diagrammatic illustration of an audio fader arrangement in accordance with the present invention.

FIG. 4 presents an embodiment of audio output switch 023 consistent with the invention. Audio output switch 023 includes a fader arrangement 060 which receives as inputs auxiliary audio 013, audio messages 024, and an interrupt control 059. Audio output switch 023 also includes an audio output device 061 which provides audio output switch 023 its only output, audio output 003.

Audio output switch 023 functions as follows. In the absence of interrupt control signal 059 but in the presence of auxiliary audio 013, the fader arrangement 060 connects the incoming auxiliary audio 013 to audio output device 061 which provides an appropriate audio output signal to audio output 003.

In the cases where either auxiliary audio 013 or audio messages 024 signal strengths are correct to drive whatever sound producing device, for example, but not limited to headphones or a speaker, the user has connected to audio output 003, audio output device 061 simply passes its input through to audio output 003. If, however, auxiliary audio 013 or audio messages 024 requires amplification or attenuation, this signal modification is provided by audio output device 061 as appropriate to the listening device the user is employing.

In the presence of interrupt control signal 059, fader arrangement 060 interrupts the flow of auxiliary audio 013 to audio output device 061 and passes audio messages 024 as received until the interrupt control signal 059 is removed. While for this embodiment, the use of an interrupt control signal 059 is described, this is not a requirement of the invention. It may be the case that the presence of audio messages 024 serve as the equivalent of the interrupt control signal 059. In this case, whenever audio message 024 is present, it has the effect on fader arrangement 060 of causing it to interrupt the auxiliary audio 013 and pass only audio messages 024 to audio output device 061. The absence of any audio message 024 would also have the effect on fader arrangement 060 of ceasing to interrupt auxiliary audio 013 and passing the auxiliary audio 013 to audio output device.

The principal advantage of audio output switch 023 is in integrating information from two sources, for example, information about exercise activity with motivational or entertainment programming. With this arrangement, the user can plug in an audio device like a portable tape player and listen to it through the fitness monitor's earphone or speaker. When the fitness monitor needs to "speak" to the user, it interrupts the external audio and takes over the earphone or speaker.

Fitness Assessment Arrangement 017

Although we have described fitness assessment arrangement 017 as being included in the overall fitness monitor 001, this is not a requirement of the invention. Instead, fitness assessment arrangement 017 may be used separately and independently of the overall fitness monitor 001.

Figure 5:
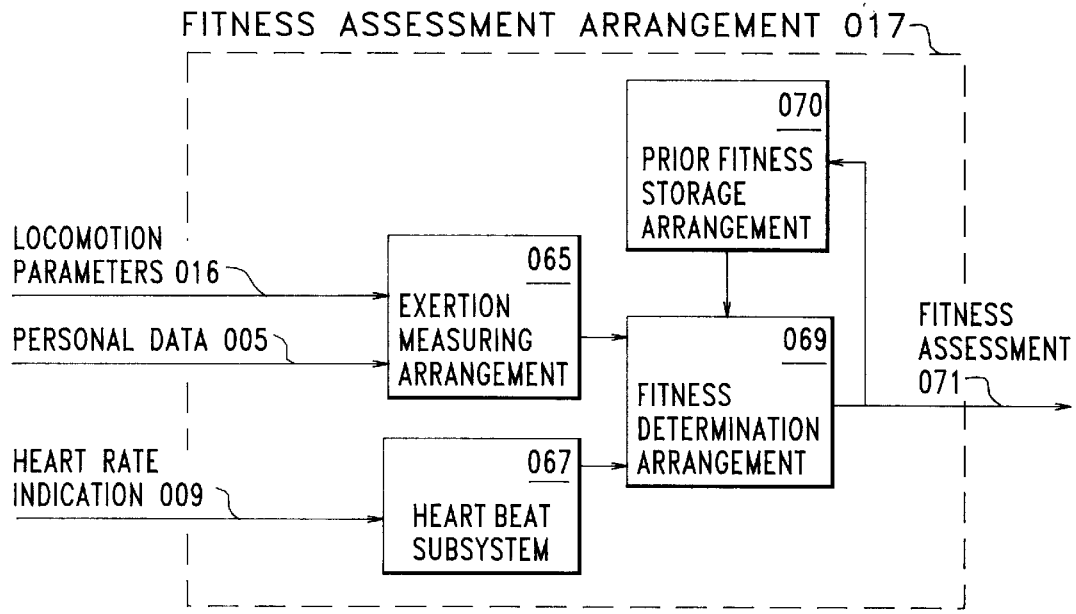
FIG. 5 is a diagrammatic illustration of a fitness assessment arrangement in accordance with the present invention.

FIG. 5 presents an embodiment of a fitness assessment arrangement 017 designed in accordance with the invention. Fitness assessment arrangement 017 includes an exertion measuring arrangement 065, a heart beat subsystem 067, and a fitness determination arrangement 069.

Exertion measuring arrangement 065 receives as input locomotion parameters 016. These locomotion parameters 016 are used in a simple linear regression relating speed of travel and gait to expended energy. Separate regressions are used for walking and running with the appropriate regression being selected based on the gait parameter passed in signal 016.

It is not a requirement that the input to the exertion measuring arrangement 065 include or be limited to outputs from pedometer 015 and personal data 005. For example, user exertion could be computed from a real-time video of the user's activity, from the disturbance of an electrical field surrounding the user, from a calorimeter, from respiratory gas exchange of $CO_{2\ for\ O_2}$, or from any other conceivable way of detecting the movements and efforts of the user.

It is conceivable that signal 016 might already contain an exertion measure. In this case, exertion measuring arrangement 065 is not a requirement of the invention, as the output of 065 would be the same as its input. For example, a cycle ergometer could input to fitness assessment arrangement 017 the user's expended energy directly as ml of oxygen per kilogram per second, requiring no further calculations before this value is passed on to the fitness determination arrangement 069.

The user's heart rate is detected by heart beat subsystem 067 through any common method of accurately measuring the current, instantaneous heart rate of an individual, as represented by beats per minute.

The exertion output of exertion measuring arrangement 065 and the heart rate output of heart beat subsystem 067 provide synchronized and simultaneous inputs to the fitness determining arrangement 069 which comprise a continuous stream of pairs of exertion and heart rate values. In the case of fitness monitor 001 described above, this time series is synchronized around each step taken by the user, but this is not a requirement of the device. Given suitable locomotion parameter 016 and heart rate 009 signals, the time series of exertion and heart rate might be synchronized around each second, 10-second period, heart beat, breath, or other suitable repeated marked interval of time.

Fitness determination arrangement 069 takes as input the simultaneous time-synchronized outputs from exertion measuring arrangement 065 and heart beat subsystem 067 and produces a fitness assessment 071 representing the user's fitness at the current date, where fitness is expressed in standard units of expended energy, such as METs. In fitness monitor 001, the time series of points used in this determination is that associated with the totality of steps taken during an exercise session on a given day. However, this is not a requirement of the invention. The time series used might simply be the previous arbitrary number of exertion/ heart rate pairs, for example, but not limited to, the previous 1000 such points.

The method of computation of fitness is as follows, hereinafter described in greater detail in conjunction with FIG. 17. First, the user's maximum heart rate, is computed from gender and age using well-known formulas. Next, a linear regression is fitted to the time series of heart rate and energy expenditure points. Using this regression, the value of energy expenditure associated with the user's max heart rate is computed. This value is the user's estimated maximum aerobic energy expenditure, which is taken as the user's aerobic fitness value.

Fitness assessment 071 may be made more accurate by taking account of the fact that changes in the heart rate occur at some time lag after changes in exertion. Correction for this lag may be made by a variety of standard time-series statistical means, or by relating the heart rate to stable periods of exertion, or by prompting the user to change exertion level.

Fitness assessment 071 does not have to be an estimate of maximal aerobic energy expenditure. It could instead be based on the ratio of heart rate to energy expenditure at some standard level of energy expenditure, or at some standard level of locomotor speed, in accordance with a number of accepted measures used in exercise physiology.

Fitness assessment 071 is expressed both quantitatively and qualitatively. The quantitative measure of fitness is expressed in appropriate units. The units that are used is not a requirement of the invention. Appropriate units include ml of oxygen per kilogram per minute, calories per minute, Watts, Ergs, or METs. The qualitative expression is the relative placement of an individual against the population norm of individuals of similar age and gender. In the preferred embodiment, the normative scale used is that of the YMCA's, but any suitable scale may be used. The scale used in the present embodiment is: excellent, very good, good, above average, average, below average, and poor, with further subdivisions of each category to provide better fitness discrimination, 27 fitness categories in all. Before reporting the qualitative fitness to the user, a hysteresis adjustment is made by software. That is, when the user's fitness is near the boundary between two fitness zones, an adjustment is made so that minor fluctuations in fitness do not result in reporting the user's qualitative fitness assessment 071 as oscillating between the two zones, such as "good" to "very good" on successive days of use. Such an oscillation would erroneously imply a large qualitative change between "good" and "very good" based on only a very small quantitative change between the values associated with the top of the "good" region and the bottom of the "very good" region.

Therefore, a requirement is imposed on the determination of the qualitative fitness zone to be reported when fitness is increasing that, if the next higher zone is to be reported, its underlying quantitative measure must exceed the boundary between adjacent fitness zones by a given amount. Similarly, the boundary must be exceeded by a given amount when fitness is decreasing. In order to make these determinations, it is necessary for to refer to the previous qualitative fitness determination. Thus, the fitness determination arrangement 069 retrieves this prior day's fitness zone by reference to a prior fitness storage arrangement 070.

While the preferred embodiment provides both quantitative and qualitative assessments of fitness, this is not a requirement of the invention. The reporting of either quantitative or qualitative assessment of fitness is in accordance with this invention. Further, the reporting of either quantities with certainties, probabilities, caveats, or conditions is also consistent with the invention.

The above described embodiment of fitness assessment arrangement 017 was developed for persons walking or running. However, this is not a requirement of the invention. If exertion measuring arrangement 065 is suitably constructed to measure the exertion associated with golfing or bicycle riding or any of the wide variety of modes of exercise, these modes of exercise are consistent with the invention as a method of determining aerobic fitness. Also to be included as possible modalities of exertion are those associated with normal everyday living, including but not limited to sleeping, lying, sitting, moving about the home or office, or climbing stairs. Also to be included in exertion would be psychological stresses that have an impact on the cardiovascular system, such as but not limited to conflict, fright, time pressure, or the opposite of such stresses, such as liberty, leisure, love, or joy.

The principal advantage of this method of fitness determination is that it is made in the course of a normal workout, walking or running, without the requirement of the execution or conduct of a prescribed and particular fitness assessment protocol, such as a timed quarter-mile run, a cycle ergometer test, or a step test, all common means in the literature of assessing an individual's fitness. The present invention with which personal fitness monitor 001 is consistent, gets a new data point with each step, so that a linear regression or other suitable statistical procedure on all those points yields a fitness estimate.

A further advantage of fitness assessment arrangement 017 is that because the fitness estimate is based on more data points, it is statistically more reliable than protocol-based estimates. Since a new estimate can be made each day, without any inconvenience to the user, smoothing across the daily estimates makes them even more reliable and useful.

A final advantage is that due to the convenience of making fitness assessments 071 on a daily basis, it is possible to accrue a day-by-day time series of fitness assessments 071 thus enabling the possibility of making a fitness prediction of likely future fitness levels based on current and recent fitness levels as described next.

Fitness Prediction Arrangement 019

Although we have described the fitness prediction arrangement 019 as being included in the overall fitness monitor 001, this is not a requirement of the invention. Instead, the fitness prediction arrangement 019 may be used separately and independently from fitness monitor 001.

Figure 6:
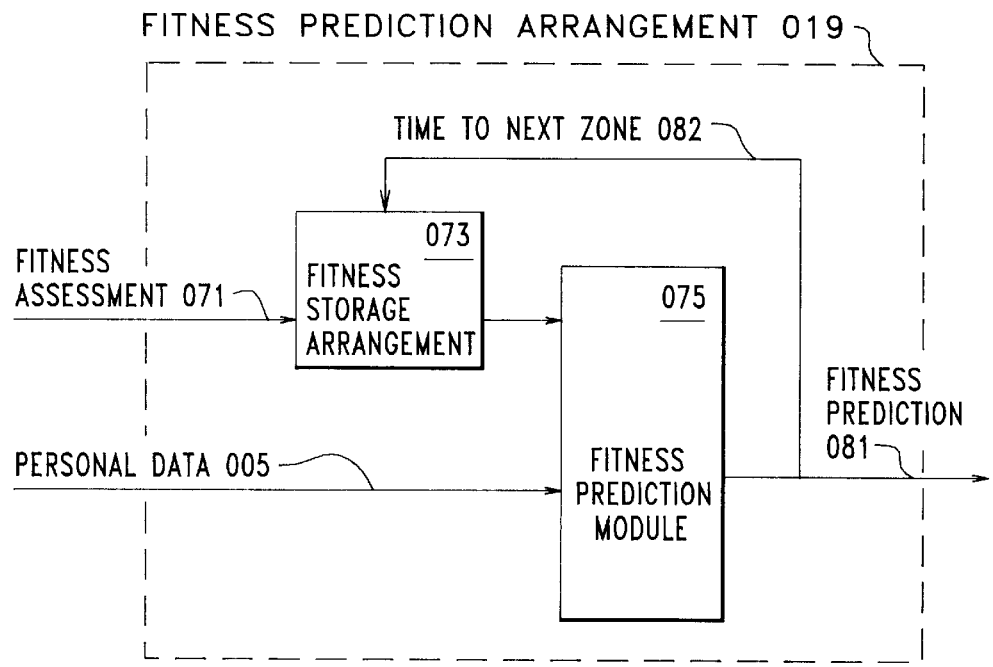
FIG. 6 is a diagrammatic illustration of a fitness prediction arrangement in accordance with the present invention.

FIG. 6 represents an embodiment of a fitness prediction arrangement 019 consistent with the invention. Fitness prediction arrangement 019 includes a fitness storage arrangement 073 and a fitness prediction module 075. Fitness prediction arrangement 019 has two inputs. The first is fitness assessment 071, which represents an individual's fitness at a given point in time as a pair of numbers: user's fitness and the associated date. The second is personal data 005, which includes information about the user's age and gender. Fitness storage arrangement 073 is so constructed to store fitness/date pairs over the course of weeks, months, or years. Fitness prediction arrangement 019 produces as its output a fitness prediction 081.

Upon receipt of a new fitness assessment 071, the fitness prediction arrangement 019 adds the incoming fitness assessment 071 to fitness storage arrangement 073 and causes a new fitness prediction 081 to be computed and output by prediction mechanism 075.

In one preferred embodiment of fitness prediction arrangement 019, the best fit to an exponential decaying curve of the set of fitness/date pairs in the fitness storage arrangement 073 is determined. This fitness trend curve is used because of the simple observation that, at a sustained daily level of routine exercise, aerobic fitness will eventually level off, so the curve flattens out.

As a refinement, the more recent days' fitness assessments 071 receive greater weight in this determination. Data more than 100 days old is not used. This embodiment also has means of fitting the fitness/date pairs using exponential growth or linear fitting models. An appropriate model is selected based on the nature of the data with the model selected having the best fit or making the most reasonable prediction of future fitness.

The user's fitness trend curve, as established by fitness prediction module 075, is projected for the upcoming 100 days, hereinafter further detailed in conjunction with the discussion of FIG. 17. Upon this curve is overlaid the 27 normative fitness zones as described for the fitness assessment arrangement 017. Thus, for a climbing trajectory, the curve enters and rises through a series of fitness zones, perhaps leveling off in one of them before reaching the next. The user's personal data 005 is used as input in selecting the proper set of norms as they depend on age and gender.

Having thus projected the user's quantitative future fitness over qualitative standardized zones, the fitness prediction arrangement 019 then identifies in how many days into the future the user's predicted fitness will cross into a new qualitative fitness zone. In one preferred embodiment, the number of days until the user's fitness crosses into the next higher or next lower zone is used as the basis of the fitness prediction 081. This number of days is stored as an additional item in the fitness storage means, that is, the days-to-next-zone.

At this point, in the embodiment being described, the user's fitness progress is reported as fitness prediction 081 as the number of days until the next fitness zone will be accessed. The number of days is expressed qualitatively, as "a day or so," "a few days," "a week or so," "a few weeks," "a month or so," and "a few months." A hysteresis adjustment similar to that described above for the fitness assessment arrangement 017 in the case of reporting qualitative fitness is used to safeguard against oscillations between, for example, "a month or so" and "a few months" in those cases where the time to next zone quantitative measure is on the border between these two qualitative time zones. To accommodate this hysteresis mechanism, the prior day's time to next zone 082 qualitative expression is stored in the fitness storage means 073.

In addition to reporting the qualitative time predicted until the next qualitative fitness category is attained, in this embodiment, fitness prediction 081 also indicates whether the fitness is rising or falling or staying level, or whether there is insufficient data to make a determination.

The attributes of the embodiment described above regarding fitness prediction 081 are consistent with the invention, but not required. All that is required is some indication of the user's fitness level, no matter how arbitrarily simple or complex, and no matter the modality of expression, including but not limited to audio, LCD display, tones, or electrical signal.

The advantages of fitness prediction arrangement 019 is that it fulfills a need that has heretofore required the services of a trained professional such as an exercise physiologist, a personal trainer, or an athletic coach to fulfill. Without the requirement of these professional services, fitness prediction arrangement 019 is able to give people a commonsense, accurate, consistent, and reliable estimation of their fitness status and progress.

Structural Description of Fitness Monitor 001

Having described fitness monitor 001 diagrammatically, and having set forth some of its objectives, attention is now directed to the fitness monitor from a structural standpoint.

Figure 7:
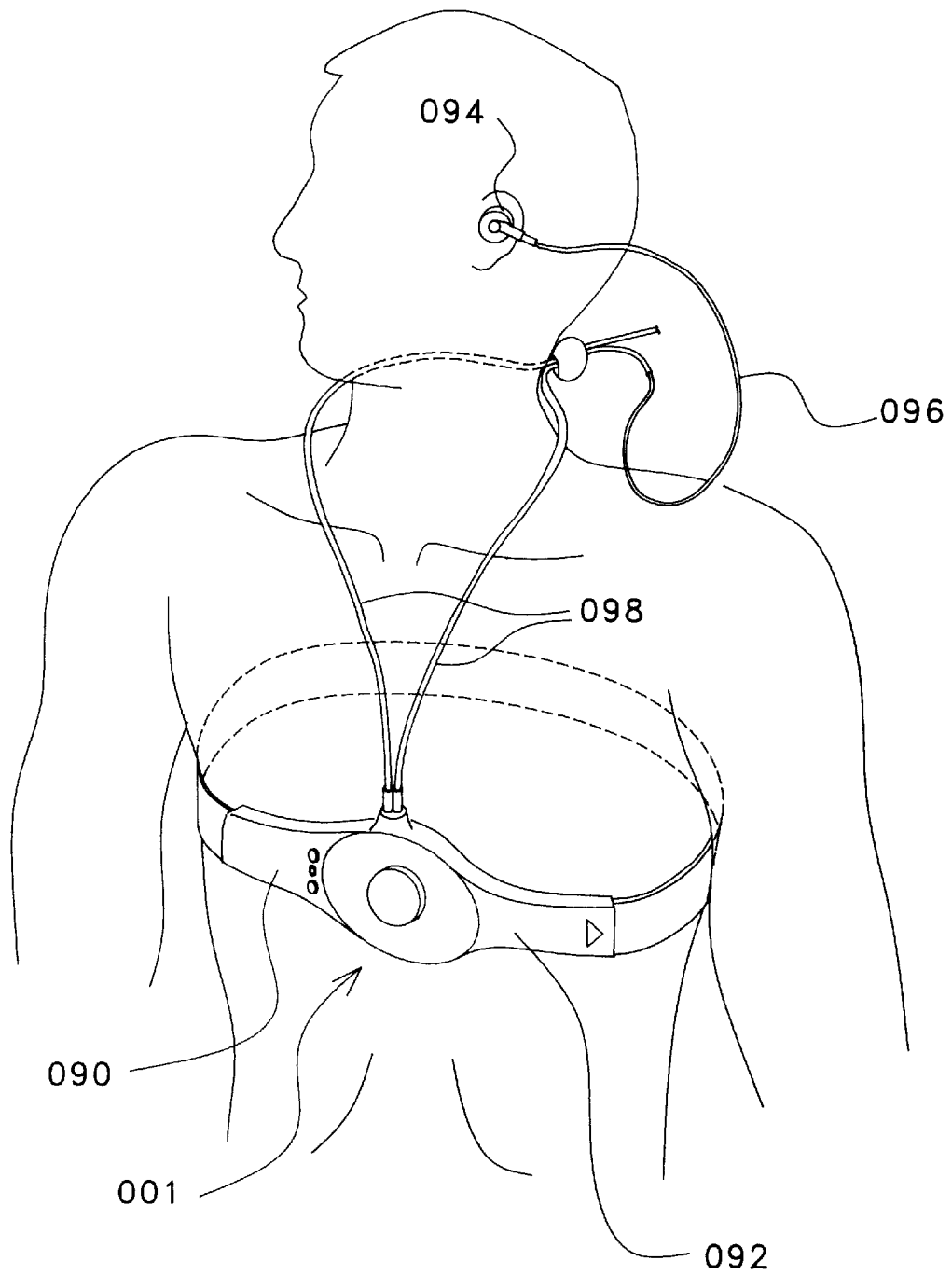
FIG. 7 is a diagrammatic illustration of another embodiment of a personal fitness monitor device in accordance with the present invention showing how the device is worn by an individual.

FIG. 7 shows how one preferred embodiment of a fitness monitor 001 invention is worn on the human body. A system housing 092 is held around the chest, just below the breasts, by an elastic chest strap 090. A two-piece neck strap 098 goes up from the system housing 092 to encircle the person's neck. An audio cable 096 comes from the system housing 092, is routed axially within one side of a neck strap 098, and exits the end of that strap to connect to an earphone 094 from which the person can hear the output of the fitness monitor.

Figure 8:
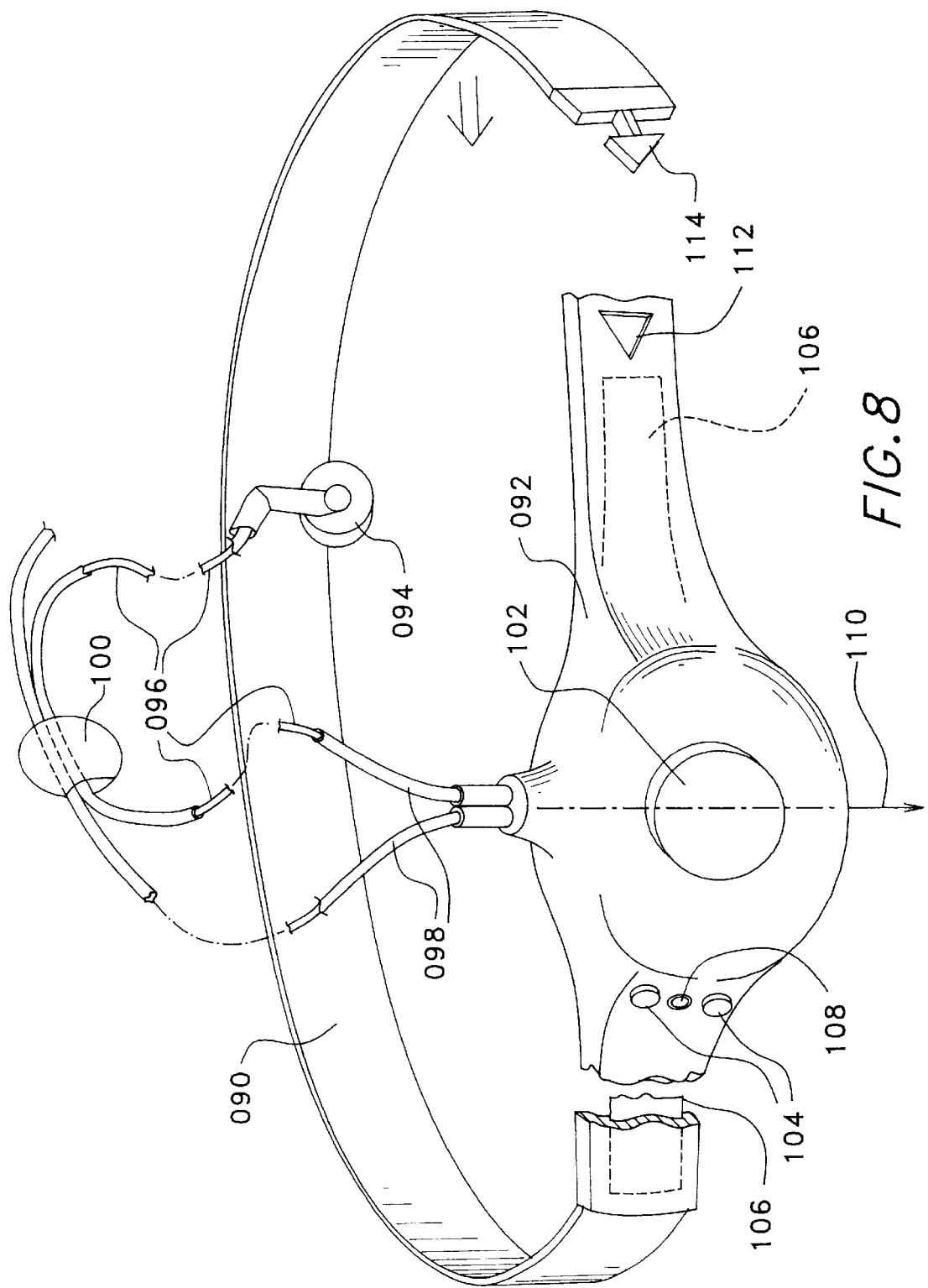
FIG. 8 is a perspective illustration of the personal fitness monitoring device of FIG. 7

Because the fitness monitor must be worn under the clothes, next to the skin, the above described design facilitates putting the fitness monitor 001 on the body. FIG. 7 and FIG. 8 illustrate how this is done. First the user makes sure that chest strap 090 is open by removing a fastener tongue 114 from a fastener slot 112. If necessary the user adjusts the length of chest strap 090 to accommodate encircling the chest snugly. With the shirt off, the user adjusts the size of the opening formed by the neck strap 098, using a sliding cinch 100. The neck strap 098 then supports the entire device while the user, with two hands free, can easily pull the end of the chest strap 090 around the body and fasten it. The user can now put on a shirt, if desired, and easily reach the audio cable 096 where it enters the neck strap 098 to pull up the audio cable 096 and place the earphone 094 in the ear. The audio cable 096 and earphone 094 deliver the audio output 003 to the ear of the user.

Continuing with FIG. 8, the surface of the system housing 092 holds two conductive plastic chest electrodes 106 against the skin. A large control button 102 on front can be felt and pressed even when covered by a shirt. As described above, the press of control button 102 is a selecting action 011. In this embodiment, two smaller volume controls 104 are used to adjust audio volume up or down. An external audio socket 108 will accept a plug from a source of auxiliary audio 013, such as a portable tape player. An accelerometer axis arrow 110 shows the placement and orientation of an accelerometer 122 within the system housing 092 (not shown in FIG. 8). The orientation is such that the acceleration of gravity is sensed as positive.

Figure 9:
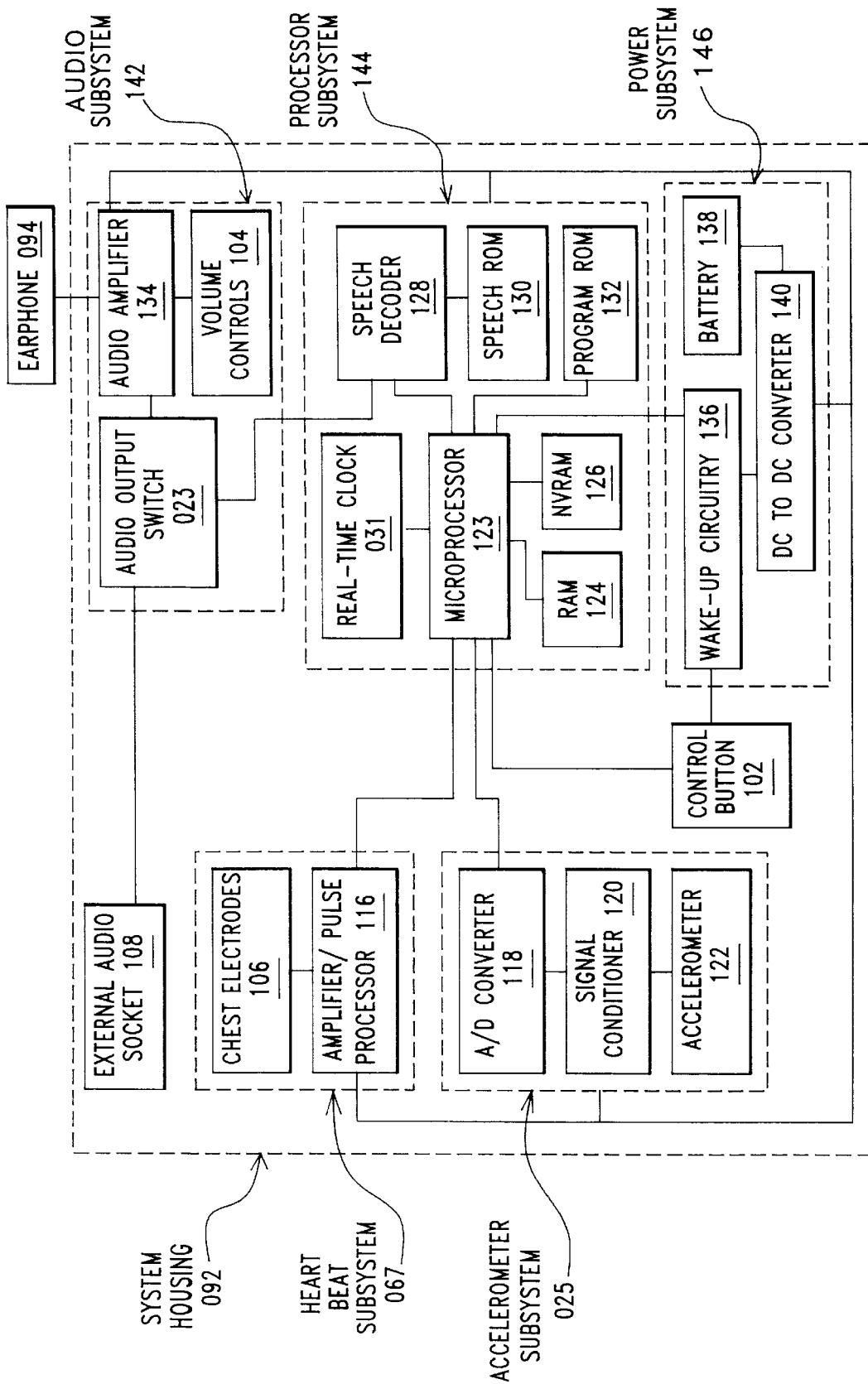
FIG. 9 is a schematic illustration showing various components which make up the personal fitness monitoring device of FIG. 7.

FIG. 9 is a diagrammatic view of the principal components in the system housing 092. Starting with the sensors, a heart beat subsystem 067 includes two chest electrodes 106 connected to an amplifier/pulse processor 116 that picks out heart beats from the voltage changes sensed by the chest electrodes 106. Chest electrodes 106 provide an embodiment of heart rate indication 009, mentioned in FIGS. 1 and 5. An accelerometer subsystem 025 consists of a readily available semiconductor accelerometer 122 whose output goes through a signal conditioner 120 and then to a single-channel A/D converter 118. The signals from the A/D converter 118 and amplifier/pulse processor 116 go to a processor subsystem 144 including an inexpensive microprocessor 123. The processor subsystem 144 has a program ROM 132 for storing executable instructions, a RAM 124 for storing computations and data during run-time, and an NVRAM 126 for storing a permanent database of facts about the user. The processor subsystem 144 also uses a real-time clock 031 for tracking data rates and the date and time that the fitness monitor 001 is in use.

A speech decoder 128 is a semiconductor device for decompressing speech data stored in a speech ROM 130, to be used for audio messages 024 to the system user. The earphone 094 is the only output device of the fitness monitor 001. Earphone 094 is connected to an audio subsystem 142 including an amplifier 134, whose volume the user can control via two button-actuated volume controls 104. An audio output switch 023 normally sends to the audio amplifier 134 any signal from an external audio socket 108, which might be connected to a personal audio device, not shown in the diagram. Whenever the fitness monitor needs to "speak" to the user, the audio output switch 023 switches off the external audio signal and routes the output of the speech decoder 128 to the audio amplifier 134.

A power subsystem 146 supplies the power from a battery 138, converted to appropriate voltage through a DC to DC converter 140, to the other subsystems of the fitness monitor 001. Wake-up circuitry 136 allows a main user control button 102 to be used to switch on the power, as well as to be used as input to the microprocessor 123 for controlling the voice menu.

In another physical embodiment, the present invention might be entirely worn on the user's head. A headband could hold an accelerometer 122 tightly, while also holding an electronics assembly and being connected to, and partially supporting, another assembly in the external ear opening. That assembly could have a pulse sensor and a combination earphone 094 and bone conduction microphone. The microphone would be there so that the user could control the system by speaking voice commands, instead of by button. The head-located embodiment would require some advances in miniaturization, a suitable model for analyzing acceleration sensed at the head, and increased reliability of ear-mounted pulse sensors. The earphone 094 and microphone combination is already available commercially.

Operational Description of Fitness Monitor 001

Having described fitness monitor 001 diagrammatically and structurally, attention is now directed to the way in which it operates.

The fitness monitor 001, or system, is worn when a person is exercising by walking or running. The purpose of the system is to observe the locomotion and heart rate of the user and translate that into useful fitness information for the user. This information is derived by computational summarizing processes on three time scales, and is kept in a permanent database of facts about the user. The processes, and their reports of fitness information, are controlled by the user's act of pressing a button in response to voiced "ear menu" current option presentations 047. The facts reported pertain to heart rate, locomotor speed, distance traveled, level of exertion, calories burned, and aerobic fitness.

User view of system functioning. To understand how the system works internally it will help to first see how the system functions from the user's point of view. To the user, the system always communicates by voice, and accepts both prompting and responses from the user when the user presses control button 102. This embodiment of user interface 021 we call the "ear menu." An example of how a person makes an ear menu selection will be described later with reference to FIG. 16. Sometimes the system "volunteers" information, and sometimes it requests information by offering a series of ear menu current option presentations 047. The user often elicits ear menu current option presentations 047 by pressing the control button 102. The only control of the system that does not occur by the ear menu is when the user raises or lowers the audio volume using the volume controls 104.

The system starts functioning when the user first presses the control button 102, which causes power to come on and the software to start running. At the system's first session of use, the system informs the user that it needs some personal data 005 about the user, and presents the user with current option presentations 047 to select appropriate values for the information. Once the user is thus identified to the system, and the system is properly placed on the body, the user can begin an exercise session. At this time, and upon all subsequent occasions when the system is turned on, the session begins either when the user presses the control button 102 and selects a menu choice to start, or whenever the user has taken some fixed number of steps. In either case the system greets the user to confirm that a session has started. A session can end implicitly, if and when the user stops locomoting for a fixed period of time, or explicitly, if selected as a menu choice.

Between the beginning and end of the session, any of the following may happen at any time. The system may initiate certain kinds of reports called "alarms." The reports may indicate whether the heart rate or speed is out of a selected range, or whether a fixed distance increment called a "milepost" has been traveled. The user may request certain reports by pressing the control button 102 and selecting the reports desired. Period reports summarize a selected period of time, such as the current moment, or the current or most recent day, week, or month. History reports indicate changes over a period of time. At any time, the user may also request that reporting preferences or alarm parameters be changed, or that the system let him/her change personal data 005, such as weight or age.

At the end of a session, the system asks if the user wants a daily summary report, delivers that report if wanted, and then shuts off. To use the system again the user must again press the control button 102 to power up the system and start its internal software.

System data flow overview. An overview of the system software is given as a data flow diagram in FIG. 10. In this diagram:

component processes are shown as circles,
sources and destinations of data at the boundary of the system are shown as rectangles,
system memory components or "data stores" are shown as pairs of parallel horizontal lines, and
data exchanged, or "flowing" between these elements is shown as arrows labeled with the names of data items exchanged.

Figure 10:
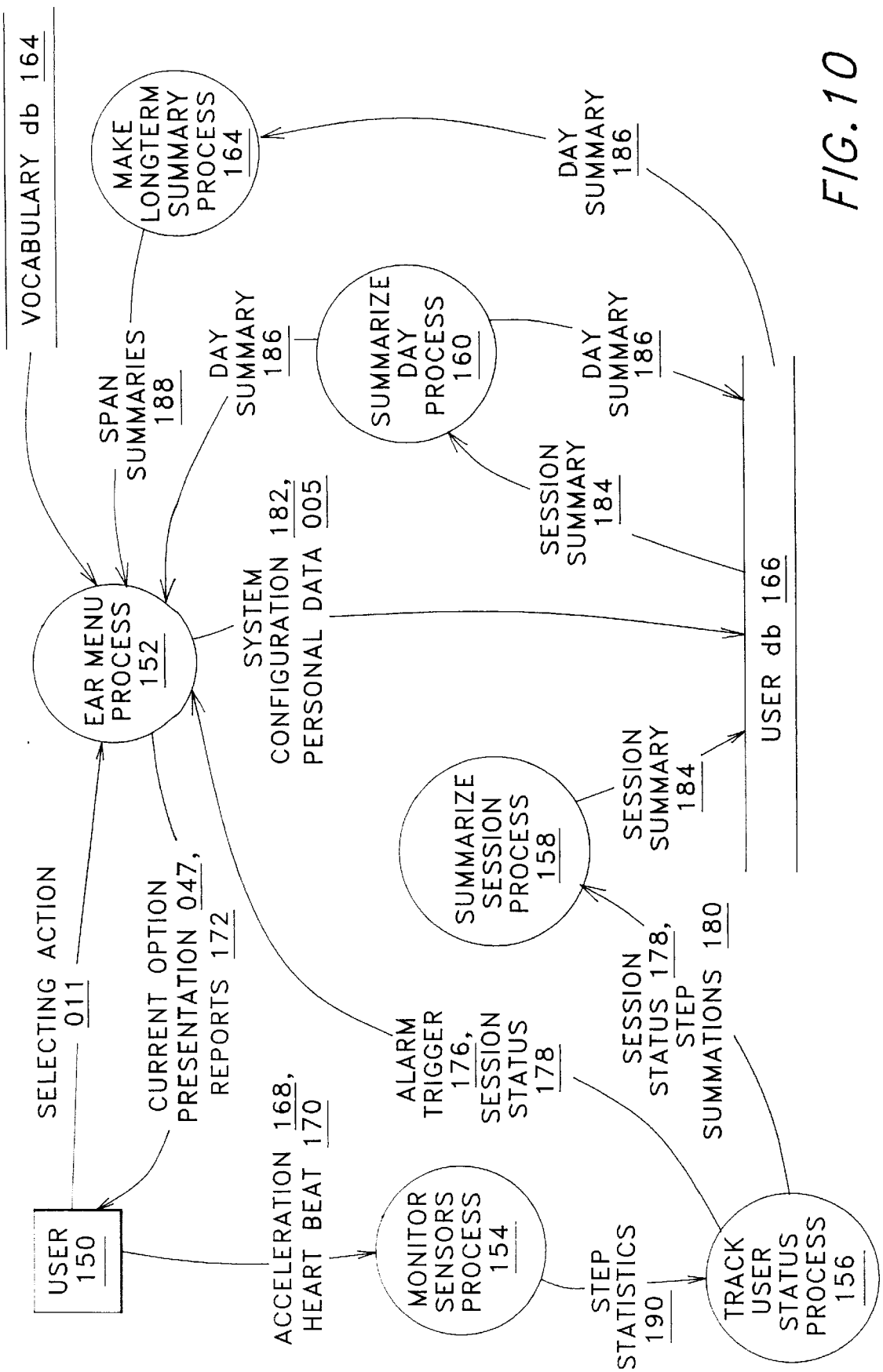
FIG. 10 is a data flow diagram illustrating the operation of the personal fitness monitoring device of FIG. 7.

Beginning at the left of FIG. 10, a system's user 150 physically generates heart beat 170 and acceleration 168 data, which are detected as outputs of the heart beat subsystem 067 and acceleration subsystem 025 (described above and shown in FIG. 9) and summarized by the monitor sensors process 154. The user 150 also generates selecting action 011 events by pressing the control button 102. These events are used by an ear menu process 152 to initiate utterances and select choices. The ear menu process 152 in turn delivers verbal messages about current option presentations 047 and reports 172 to the user 150. The ear menu process 152 assembles its messages using codes for verbal elements from a vocabulary database 164 that is held in speech ROM 130 hardware (shown in FIG. 9). For its messages to be heard, the ear menu process 152 must make requests for the verbal elements to be turned into sounds via the speech decoder 128 and the audio subsystem 142 hardware. Given a request from the user 150, the ear menu process 152 may update a user database 166, held in NVRAM 126 hardware. These updates may be either the user's preferences for system configuration 182, or elements of the user's personal, physical information, called personal data 005. The ear menu process 152 may also request from other processes data that it uses for making various reports 172, as will be described below.

The monitor sensors process 154 summarizes its inputs for each locomotor step or period of rest and passes these as step statistics 190 to a track user status process 156. That process accumulates data about the session in RAM 124. The track user status process 156 also sends to the ear menu process 152 alarm trigger 176 data that cause the ear menu process 152 to issue one of the alarm reports 172 described hereinafter in Table 2. Given a request from the ear menu process 152, the track user status process 156 will send to it session status 178 data that indicate what the user 150 is currently doing. Those data will be used by the ear menu process 152 to make an immediate report, also described in Table 2.

Once the user 150 makes an explicit or implicit choice to end the session, the track user status process 156 sends to a summarize session process 158 a current session status 178 and some statistical summaries of heart rate and energy expenditure, called the step summations 180. The summarize session process 158 uses these data to compute an aerobic raw fitness, based on the regression between the heart rate and energy expenditure over the whole session, then moves a summary of fitness and activity called a session summary 184, from RAM 124 to the user database 166 that is held in NVRAM 126.

A summarize day process 160 is required because someone may have multiple exercise sessions in a day. If the user 150 requests a summary of results "so far today", then the summarize day process 160 uses the session summary 184 data in the user database 166 to summarize the activities of the day in a day summary 186. The day summary 186 is in turn used by the ear menu process 152 to voice a day summary report described in Table 2. The summarize day process 160 also executes whenever the first session of a day begins, because it is then clear that the last day of use before the present one is finished. All session summaries 184 of that last day of use are summarized and stored as a day summary 186 in the user database 166. Any intervening days in the user database 166 are given "null" day summary 186 data indicating that the fitness monitor 001 was not used in those days. The summarize day process 160 also computes the user's fitness trend, as part of the day summary 186 for the user database 166. The procedure for computing the fitness trend is an embodiment of the fitness prediction module 075 described earlier in FIG. 6. The fitness trend is based on fitting a fitness trend curve to the raw fitness data in the user database 166 for, at most, the previous 100 days. The curve-fitting process produces data characterizing the fitness trend. This becomes part of the day summary 186.

A make long-term summary process 162 uses day summaries 186 from the user database 166 to summarize activities and fitness for various spans of time in the form of span summaries 188. It sends these span summaries 188 to the ear menu process 152. The ear menu process 152 uses these summaries to make: a prior week report, a prior month report, a distance history report, an energy history report, and a fitness history report. Examples of all these reports 172 are shown in Table 2.

The next six sections of this specification examine the details of each of the six processes in FIG. 10.

Figure 11:
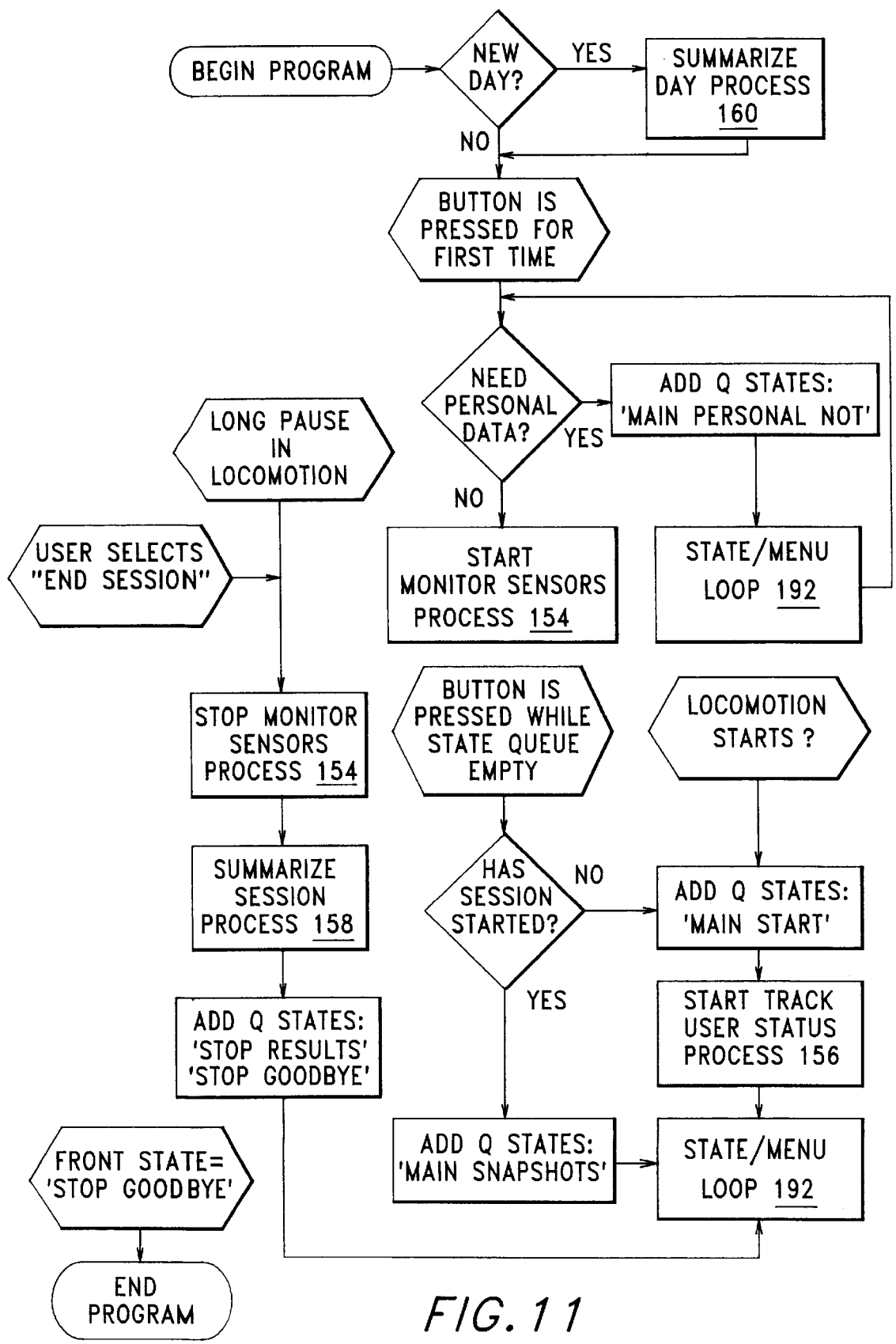
FIG. 11 is a flow chart illustrating one embodiment of an ear menu process of the personal fitness monitoring device of FIG. 7.

Ear Menu Process 152 Details. The ear menu process 152 may be considered the master control process of the fitness monitor 001. Most of its decision logic and control over the system's vocal utterances is carried out using a state queue 191, as demonstrated later in FIG. 16. State queue 191 is processed by a state/menu loop 192, described later by using FIG. 9. In FIG. 11 we show how the system starts up and shuts down via the ear menu process 152. When the system starts the real-time clock 031 is consulted and the time compared to the last session time in the user database 166 to see if this is the first session of a new day. If so, all the sessions of the previous day are summarized by the summarize day process 160.

No further action is taken until the control button is pressed for the first time. The system checks the user database 166 to see if it is missing any personal data 005 from the set of the user's body weight, body height, leg length, age in years, and sex. If any are missing then a state, 'main personal not' is added to the state queue 191 by an add q states routine, and the state/menu loop 192 is entered. The effect of this is to engage the user in a menu-driven dialogue to obtain the missing items. The state/menu loop 192 is described later in discussing FIG. 12, and the dialogue is described later in discussing Table 1. Once all personal data 005 are available, the system starts the monitor sensors process 154. Without the personal data 005, the monitor sensors process 154 would not be able to analyze locomotor steps or track energy expenditure 228.

Once the monitor sensors process 154 is underway, one of the following three events will be dealt with by the ear menu process 152:

There is a long pause, for example five minutes, with no locomotion detected. This is assumed to mean that the user failed to start exercising, so the monitor sensors process 154 is stopped, to stop the flow of incoming data; the summarize session process 158 is called, and two states are placed on the queue: 'stop results' and 'stop goodbye'. The system then enters the state/menu loop 192, in which the 'stop results' state causes the system to ask the user whether to make the day summary report. Once the report is made or skipped, the 'stop goodbye' state becomes the front state in the queue, causing the system to utter a goodbye message and then power itself down. Utterances for these two steps are shown in the WHEN SESSION TERMINATES section of Table 1.

The control button will be pressed while the state queue 191 is empty. If the exercise session has not already started, this is taken as a request from the user to start the session, so the state, 'main start' is placed on the queue and the track user status process 156 is started. The system then enters a state/menu loop 192, which causes a greeting to be issued, as in the WHEN SESSION BEGINS row of Table 1.

Locomotion will be detected as starting by the monitor sensors process 154 having detected a predetermined number of steps in a row. Subsequent events are the same as if the control button 102 was used to start the session.

Some subsequent button presses will occur while a choice is in the state queue 191, and will thereby be used by logic in the state/menu loop 192. Other button presses will occur when the state queue 191 is empty. These are taken as a kind of interrupt by the user to get the system's attention, so the state 'main snapshots' is added to the queue. When the state/menu loop 192 then executes, the 'main snapshots' state causes the dialogue shown in Table 1, in the row called BUTTON PRESS AFTER SESSION IS LAUNCHED, BUT WHEN NO UTTERANCE IS ONGOING.

Any time after the session has started one of two events can happen that lead to the system ending its execution. One is that a long pause in locomotion will be detected by monitor sensors process 154, and another is that the user selects a menu item called "End session?" In either case the logic followed to the end of the program is the same as detailed above when the user failed to start locomoting at all during the session.

Figure 15:
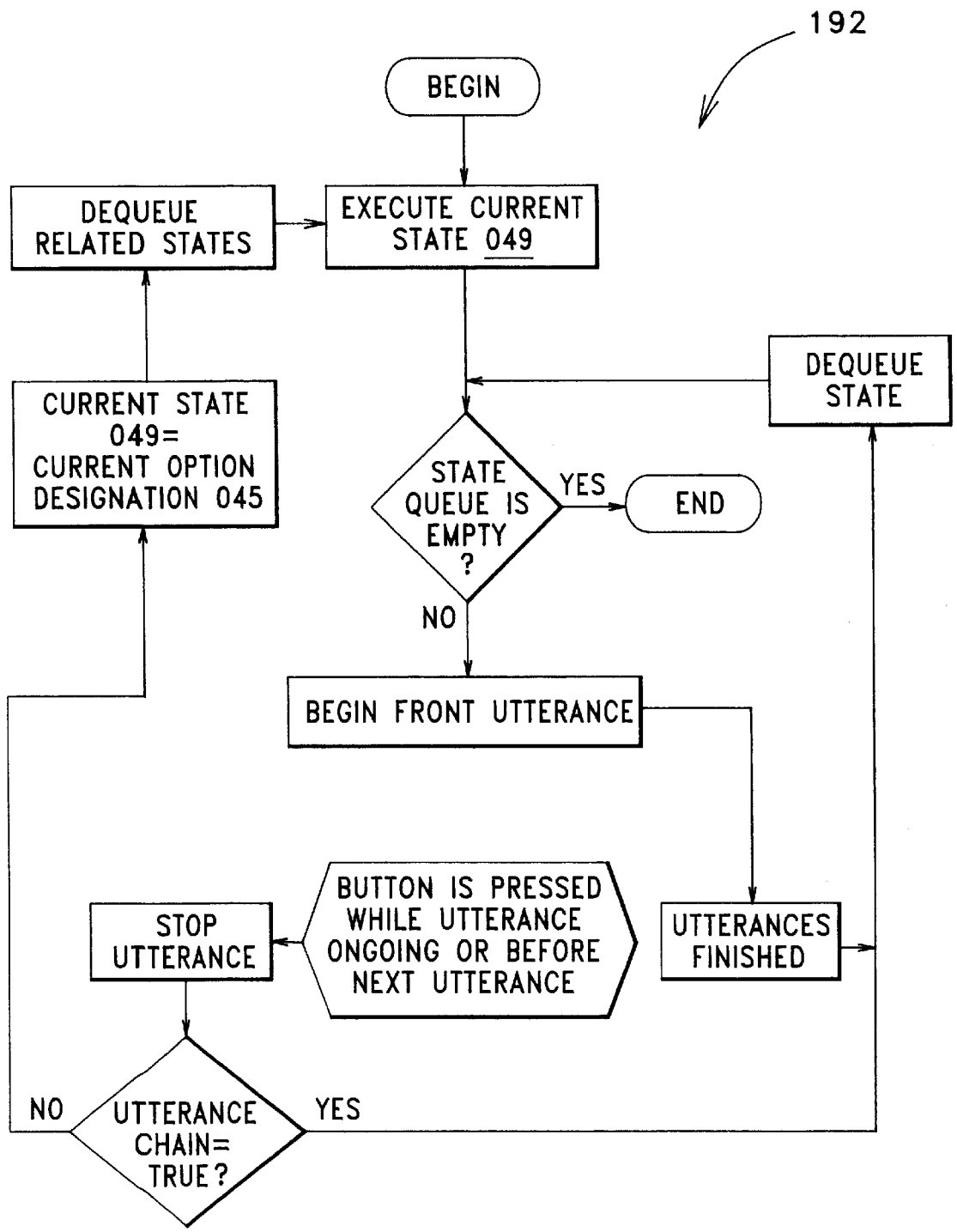
FIG. 15 is a flow chart illustrating one embodiment of a state/menu process used by the personal fitness monitoring device of FIG. 7.

FIG. 15 shows the state/menu loop 192 that is used to handle all user interaction and reporting. The loop uses a first-in, first-out state queue 191 in which named system states are associated with system utterances. Starting with begin in the diagram, when the state/menu loop 192 is called some state is at the front of the queue. Any computations required by that state, such as data summaries or queuing further states, are executed in the step called "execute current state 049". If the state queue 191 is then empty, the loop is ended. Otherwise the next state in the queue comes to the front, and the system begins speaking its associated utterance. If the utterance finishes by being spoken completely and no control button 102 press occurs before the next queued utterance, then the current state 049 is dequeued and the next state, if any, is considered. If instead the user selects the menu choice by pressing the control button 102 any time before the next queued utterance, this is considered to be a menu selection. In FIG. 15 this button press is shown as an event which leads to stopping the utterance should it still be ongoing. If the utterance had a chain attribute equal to True, then the button press is simply intended to lead to the next utterance in the queue, so the current state 049 is dequeued and the test for an empty queue is made again. If chain is not True, then the current state 049 is set to be the current option designation 045. The system then discards any states that are "related" to the current option designation 045 because they would have been offered as alternatives had it not been chosen. The loop then begins over by executing the current state's 049 processing.

Figure 16:
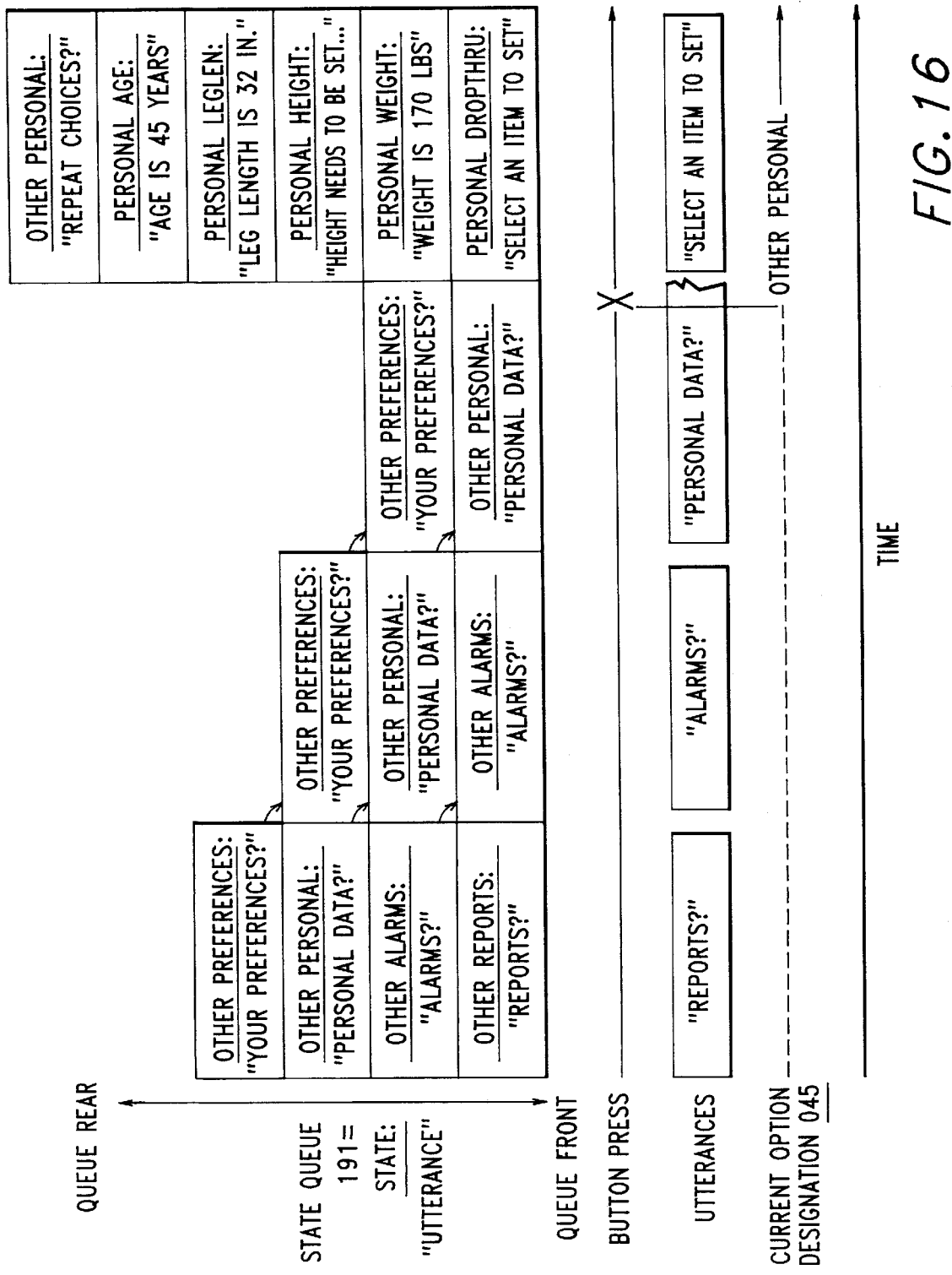
FIG. 16 is a time line illustrating the state/menu process illustrated in FIG. 15.

FIG. 16 displays the events surrounding a menu choice on a time line in order to better show how a user makes a menu selection. The top time line shows the contents of the state: utterance pairs in the state queue 191. The time line below the top shows when the user presses the control button 102 as an "X". The next time line down shows the utterances, or current option presentations 047, made by the system through the audio subsystem 142. The bottom time line shows which state is the current option designation 045. As successive utterances are made, the previous ones are de-queued. Eventually the user presses the button while the system is uttering "Personal data?". That utterance is stopped, as indicated by the broken end of the graphic, and a new state called 'other personal' is thereby chosen. The system drops the remaining related state, 'other preferences', and then, as a part of executing the chosen state, queues a series of new states in the queue. The system then presents the utterance, "Select an item to set" for the first of the new current option presentations 047. The word "dropthru" in its associated state name means that it is a chained utterance, and, even if it is selected by a button press, the ear menu process 152 will chain to the next utterance, "Weight is 170 lbs.".

The program logic included in executing the current state 049 can be arbitrarily complex, so that the state/menu loop 192 is able to handle fairly elaborate reporting procedures and menu dialogues. The system's menu dialogues are presented in Table 1, whose main rows correspond to the timing of a set of utterances or to the symbolic name of the menu in which the utterances are used.

TABLE 1

System Menu Dialogues

- Within a section, utterances are presented in order.
- System action = blank means that a press during utterance stops that utterance and starts the next.
- When an action is a report 172, verbal reports are like the examples shown in Table 2

| When Presented or Menu Name | Pre-condition or Interpretation | System utterance | System action when selected |
|---|---|---|---|
| BUTTON PRESS BEFORE SESSION BEGINS | | | |
| | if user's weight > NN days old | "Please press home now to update your weight." | go to SET WEIGHT |
| | | "Start session?" | go to WHEN SESSION BEGINS |
| | | "More choices?" | go to MORE CHOICES |
| | no button press | | wait for press or alarm |
| WHEN SESSION BEGINS | | | |
| | depends on time of day. XX is ordinal of exercise session today | "Good [ morning | afternoon | evening ]. Starting Session Number XX for today." | |
| BUTTON PRESS AFTER SESSION LAUNCHED, BUT WHEN NO UTTERANCE IS ONGOING | This section is also called an immediate report 204 in Table 2 | | |
| | XXX is current heart rate 226 | "Heart rate, XX." | skip to "End session?" |
| | X.X is miles traveled in session | "Distance, X.X miles" | skip to "End session?" |
| | XX.X is current speed or pace; choice is a user preference | "Speed, XX.X [ miles per hour | minutes per mile ]" | skip to "End session?" |
| | XXX is calories burned in session | "Calories, XX." | skip to "End session?" |
| | | "End session?" | go to WHEN SESSION TERMINATES |
| | | "More choices?" | go to MORE CHOICES |
| | no button press | | wait for press or alarm |
| LONG PAUSE IN LOCOMOTION | | | |
| | | "You have stopped moving for X minutes. I am ending your session. You can start a new session by pressing the button." | go to WHEN SESSION TERMINATES |
| WHEN SESSION TERMINATES | | | |
| | | "Would you like your results for today?" | presents day summary report 214 |
| | | "Good bye." | system powers down after this utterance |
| MORE CHOICES | | | |
| | | "Reports?" | go to REPORTS MENU |
| | | "Alarms?" | go to ALARMS MENU |
| | | "Personal data?" | go to PERSONAL DATA MENU |
| | | "Personal preferences?" | go to |

TABLE 1-continued

System Menu Dialogues

- Within a section, utterances are presented in order.
- System action = blank means that a press during utterance stops that utterance and starts the next.
- When an action is a report 172, verbal reports are like the examples shown in Table 2

| When Presented or Menu Name | Pre-condition or Interpretation | System utterance | System action when selected |
|---|---|---|---|
| | | | PERSONAL PREFERENCES MENU |
| | | "Repeat choices?" | go to "Reports?" above |
| | no button press | | wait for press or alarm |
| REPORTS MENU | | | |
| | | "Fitness update?" | presents Fitness Trend report |
| | session is in progress | "Summary of today?" | presents day summary report 214 |
| | when have data for prior week or month | "Summary of last [week \| month]?" | presents prior week report 216 or prior month report 218 |
| | | "Recent history?" | go to RECENT HISTORY MENU |
| RECENT HISTORY MENU | | | |
| | | "Pick an item to hear its trend." "Distance?" | presents distance history report 220 |
| | | "METs and calories?" | presents energy history report 222 |
| | | "Fitness?" | presents fitness history report 224 |
| | | "Repeat Choices?" | go to "Distance?" |
| | no button press | | wait for press or alarm |
| ALARMS MENU | | | |
| | | "Heart alarm?" | go to SET HEART ALARM |
| | | "Cruise control?" | go to SET CRUISE CONTROL |
| | | "Mileposts?" | go to SET MILEPOSTS |
| | | "Repeat choices?" | go to "Heart alarm?" |
| | no button press | | wait for press or alarm |
| PERSONAL DATA MENU | | | |
| | | "Select an item to set or change." | |
| | XXX if known, else needs to be set | "Weight [XXX lbs. \| needs to be set]" | go to SET WEIGHT |
| | XX if known, else needs to be set | "Height, [inches \| needs to be set]" | go to SET HEIGHT |
| | XX if known, else needs to be set | "Leg length [XX inches \| needs to be set." | go to SET LEGLEN |
| | XX if known, else needs to be set | "Age [XX years \| needs to be set." | go to SET AGE |
| | value if known, else needs to be set | Sex [male \| female \| needs to be set." | go to SET SEX |
| | no button press | | wait for press or alarm |
| PERSONAL PREFERENCES MENU | | | |
| | | "Use [pace instead of speed \| speed instead of pace] in reports?" | changes mode of presenting velocity: minutes per mile, or miles per hour |
| | no button press | | wait for press or alarm |
| SET HEART ALARM | | | |
| | if alarm is already off | "Heart alarm is off. Turn it on?" | go to next |

TABLE 1-continued

System Menu Dialogues

- Within a section, utterances are presented in order.
- System action = blank means that a press during utterance stops that utterance and starts the next.
- When an action is a report 172, verbal reports are like the examples shown in Table 2

| When Presented or Menu Name | Pre-condition or Interpretation | System utterance | System action when selected |
|---|---|---|---|
| | When heart alarm changes or is already on | "Heart alarm is on and set to [light activity \| moderate activity \| weight management \| aerobic \| anaerobic threshold \| red line]". | question |
| | | "Raise heart alarm zone?" | Raises zone 1 increment and goes to pre-condition 'when heart alarm changes' |
| | | "Lower heart alarm zone?" | Lowers zone 1 increment and goes to pre-condition 'when heart alarm changes' |
| | | "Turn heart alarm off?" | go to pre-condition 'alarm gets turned off' |
| | alarm gets turned off | "Heart alarm is off". | |
| | no button press | | state of alarm does not change. |
| SET CRUISE CONTROL | Dialogues for changing these items have been left out for brevity. | | |
| SET MILEPOSTS | | | |
| SET WEIGHT | | | |
| SET HEIGHT | | | |
| SET LEGLEN | | | |
| SET AGE | | | |
| SET SEX | | | |
| HEART ALARM 206 | | | |
| | When heart rate 226 moves in or out of chosen band. | ["Your heart rate is too high" \| "Your heart rate is in range" \| "Your heart rate is too low"] | wait for press or alarm |
| CRUISE CONTROL ALARM 208 | | | |
| | When speed (or pace) moves in or out of chosen band. | ["Your [pace \| speed] is too fast." \| "Your [pace \| speed] is OK." \| "Your [pace \| speed] is too slow."] | wait for press or alarm |
| MILEPOST ALARM 210 | | | |
| | session distance exceeds another milepost increment. X.X is in current velocity mode. | "You've just passed a [tenth mile \| quarter mile \| half mile \| mile] post, with [average speed of X.X miles per hour \| average pace of X.X minutes per mile]" | wait for press or alarm |

Table 2 gives examples of all the kinds of reports 172 that the system can make to the user about the user's activity and fitness status.

TABLE 2

Fitness Monitor Reports 172

| Report Name | Number | Example text |
|---|---|---|
| Immediate | 204 | "Heart rate, 130. Distance 1.1 miles. Speed 4.6 miles per hour. Calories 112." |
| Heart Alarm | 206 | "Your heart rate is too high." |
| Cruise Control Alarm | 208 | "Your speed is too low." |
| Milepost Alarm | 210 | "You've just passed a half post, with average speed of 3.7 miles per hour." |
| Fitness Trend | 212 | "Your latest fitness category was good, step 3, and is projected to fall to good, step 2 in a couple of months. Your fitness is 11.5 METs." |

TABLE 2-continued

Fitness Monitor Reports 172

| Report Name | Number | Example text |
| --- | --- | --- |
| Day Summary | 214 | "Averages and totals for today: elapsed time 48 minutes; distance 3.3 miles; pace 14.5 minutes per mile; heart rate 125, in the light activity zone; activity 7 METs; calories 305." |
| Prior Week | 216 | "Summary of last week.: elapsed time 156 minutes, distance 17.8 miles, speed 6.9 miles per hour, heart rate 145, in the aerobic zone, average activity level 9.5 METs, calories burned 431; Most recent fitness above average, step 2, 14 METs." |
| Prior Month | 218 | "Summary of January. 7 days of use. elapsed time 283 minutes. distance 25.5 miles, calories burned 2,808. Over the month your fitness stayed level at 10.2 METs." |
| Distance History | 220 | "Here is your distance history. Yesterday your results were: distance 2.8 miles. Since Sunday, distance 4.2 miles. Last week distance 5.5 miles. Another trend?" If selected goes back to RECENT TRENDS MENU, see Table 1. |
| Energy History | 222 | "Here is your calories history. Yesterday your results were: calories 310. Since Sunday, calories 521. Last week calories 613. Another trend?" If selected goes back to RECENT TRENDS MENU, see Table 1. |
| Fitness History | 224 | Here is your fitness history. Yesterday your results were: fitness below average, 9.7 METs. Since Sunday, most recent fitness below average, 9.7 METs. Last week most recent fitness below average, 9.8 METs. Another trend?" If selected goes back to RECENT TRENDS MENU, see Table 1. |

Speech utterances, which are either current option presentations 047 or reports 172, are either phrases or complete sentences. Each utterance may have fixed components, such as "Starting session number" and "for today", as well as variable components, such as numbers or dates. The ear menu process 152 includes logic to assemble complete utterances from pre-stored parts, such as: "Starting session number" "two" "for today". The words in these parts are pre-recorded and stored in speech ROM 130 with a fixed table of addresses. To "play" an utterance the ear menu process 152 makes an ordered list of speech addresses, fetches them in sequence from speech ROM 130, and sends them to the speech decoder 128, which in turn transforms each part into an audio signal and sends the signal to the audio subsystem 142 for playing.

In another embodiment speech utterances could instead be assembled as text strings and then converted to speech sounds through readily available text-to-speech systems. This would have the advantage of a more unlimited vocabulary for a fixed amount of memory, as well as more natural-sounding speech rhythm and emphasis. However text-to-speech words do sound less natural than pre-recorded ones. At the vocabulary size needed for the above described embodiment of the present invention, about 325 words, pre-recorded and text-to-speech require about the same amount of memory for delivery.

Should the system start to play an utterance while the user is listening, via the audio subsystem 142, to an external audio source, then the audio output switch 023 switches from the external source to the internal speech signal. When there has been no speech signal for a suitable delay period, for example 3 seconds, then the audio output switch 023 switches back to the external audio source.

Monitor Sensors Process 154 Details. This module monitors the heart beat subsystem 067 and the accelerometer subsystem 025 at a suitable sampling frequency, in order to determine (a) the occurrence of heart beats 170, and thus a heart rate 226, and (b) to determine the occurrence of footfalls that mean a locomotor step has been taken. The steps are classified as to speed and gait, and are passed on to the track user status process 156 module.

Figure 12:
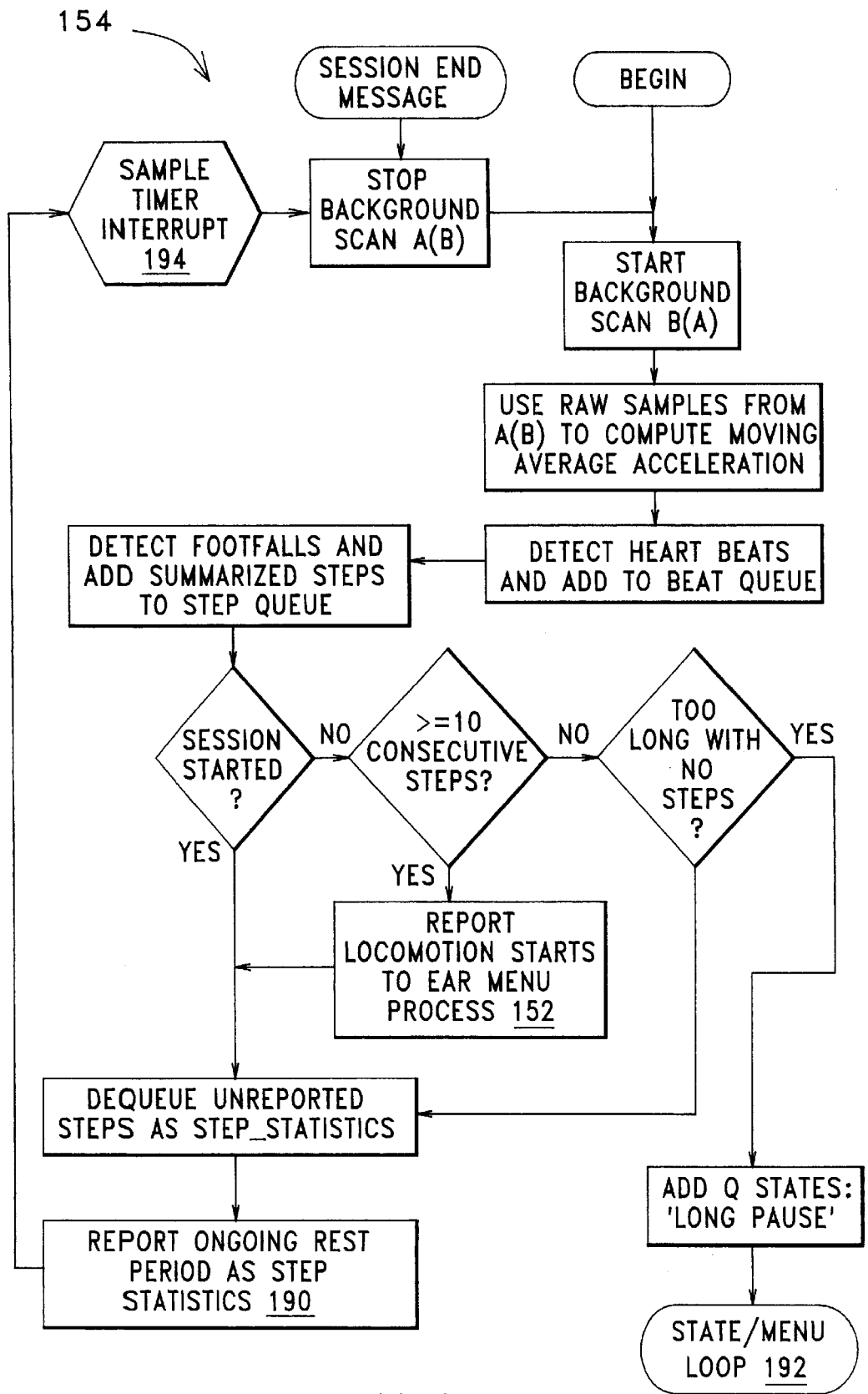
FIG. 12 is a flow chart illustrating one embodiment of a monitor sensors process of the personal fitness monitoring device of FIG. 7.

FIG. 12 shows the main processing loop for the monitor sensors process 154. When the module begins it starts a background scan of the heart beat subsystem 067 and accelerometer subsystem 025 at a suitable sampling frequency, such as 100 Hz. This scan continues until stopped later in the loop by a sample timer interrupt 194. Two buffers are maintained to hold background scans. While one buffer, A or B is being filled with data, the data in the other, B or A, is being analyzed. The first step is to compute at each sample time a moving average of acceleration 168, which serves as a baseline for describing the acceleration 168 waveform of a locomotor step. The next step is to extract the heart signal pulse peaks, convert them to beats per minute, and put them in a beat queue, ordered by time of occurrence.

Following this a loop goes through the buffer, A or B, looking for peaks of positive acceleration 168 that are indicative of footfalls. Each interval between footfalls is taken to be a locomotor "step", and is summarized and put in a step queue.

Figure 13A:
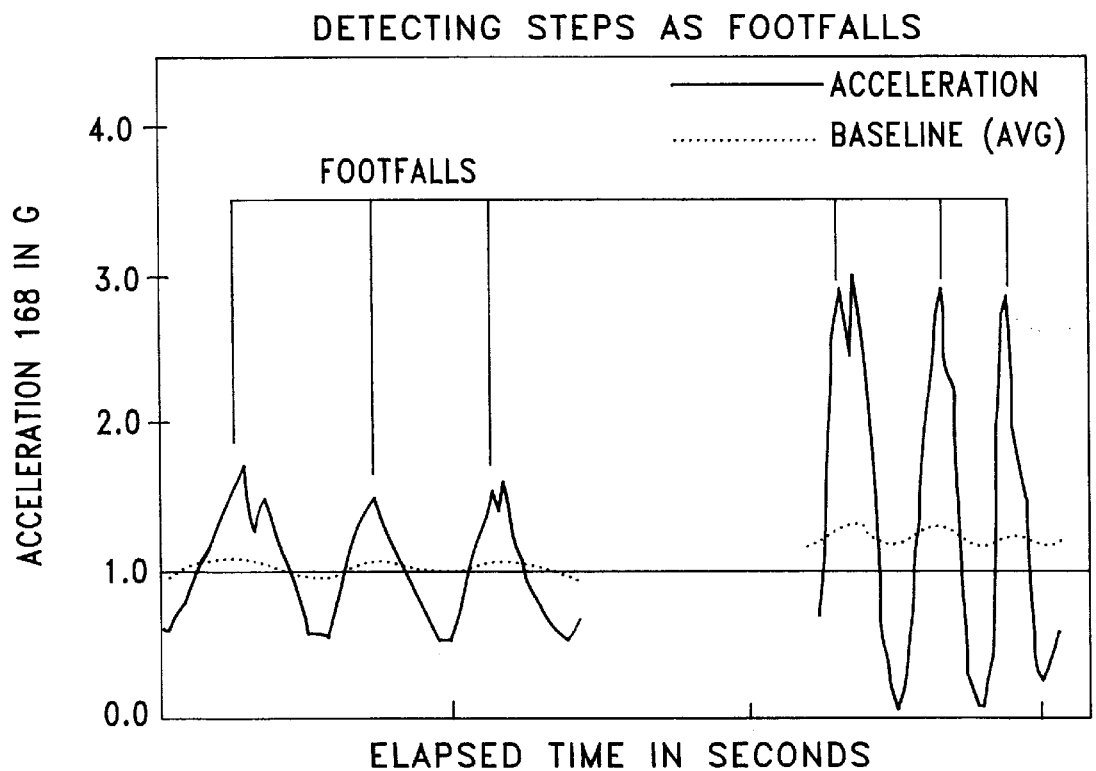
FIG. 13a is diagrammatic illustration of one embodiment detailing how the personal fitness monitoring device of FIG. 7 detects steps as footfalls.
Figure 13B:
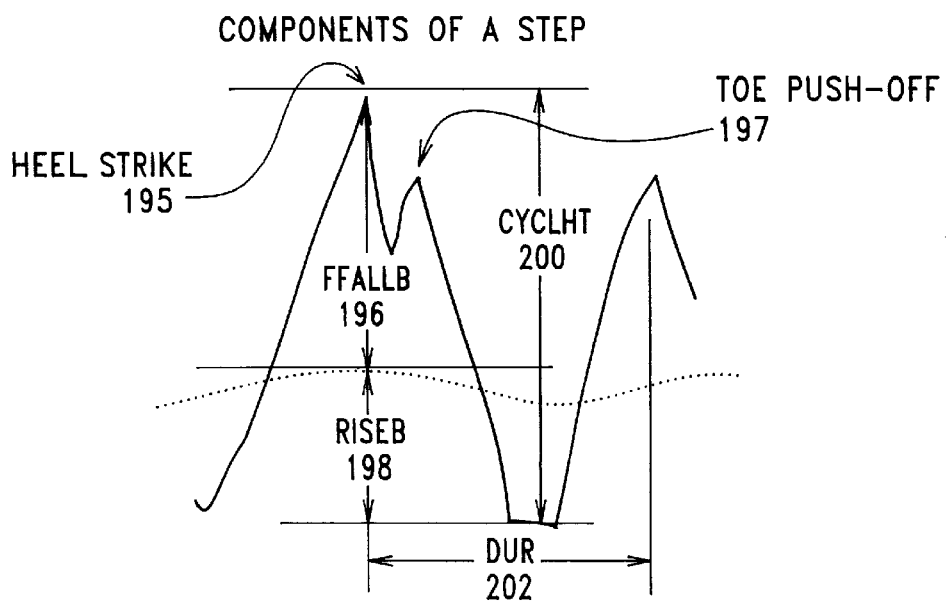
FIG. 13b is a diagrammatic illustration of one embodiment detailing the different components of a step interpreted by the personal fitness monitoring device of FIG. 7.

FIG. 13a shows typical acceleration 168 waveforms, and helps explain how footfalls are detected. If a peak has multiple sub-peaks, the first is used. Peaks occurring on the falling side of a waveform are not considered to be footfalls. Peaks that occur too soon after another peak are not considered to be footfalls. The minimum interval between footfalls is never less than 250 msec, but is adjusted upward if steps are occurring slowly, and downward if steps are occurring faster. Peaks must be above a minimum height, never less than 0.1 G above baseline, which is usually around 1 G. The minimum height is adjusted upwards when peak accelerations 168 have been higher, and is adjusted downwards when peak accelerations 168 have been lower. FIG. 13b shows that running steps produce higher peaks and more frequent footfalls per unit time.

Once each step is found, it is classified as to whether the user was running, walking or resting. The determination is based on the interval between footfalls or their inverse, the step frequency, and the height of the acceleration footfall peak, using rules shown in the following, Table 3.

TABLE 3

Gait criterion rules used in gait model 030

| Gait | Criterion |
|------|-----------|
| rest | interval between footfalls >= 2500 msec |
| walk | (step frequency in Hz + footfall in G) <= 5.0 |
| run  | (step frequency in Hz + footfall in G) > 5.0 |

For each locomotor step the software also makes an independent estimate of the user's velocity. FIG. 13b shows how step parameters are derived to aid this process. The ffallb 196 is the height of the acceleration peak above the baseline average acceleration, shown as a dotted line. The riseb 198, so named because it reflects the rise of the body during the step cycle, is measured as the depth of the lowest point of the cycle below the initial baseline. The cyclht 200 is the sum of these two, and the dur 202 is the duration in msec between footfalls.

Figure 14:
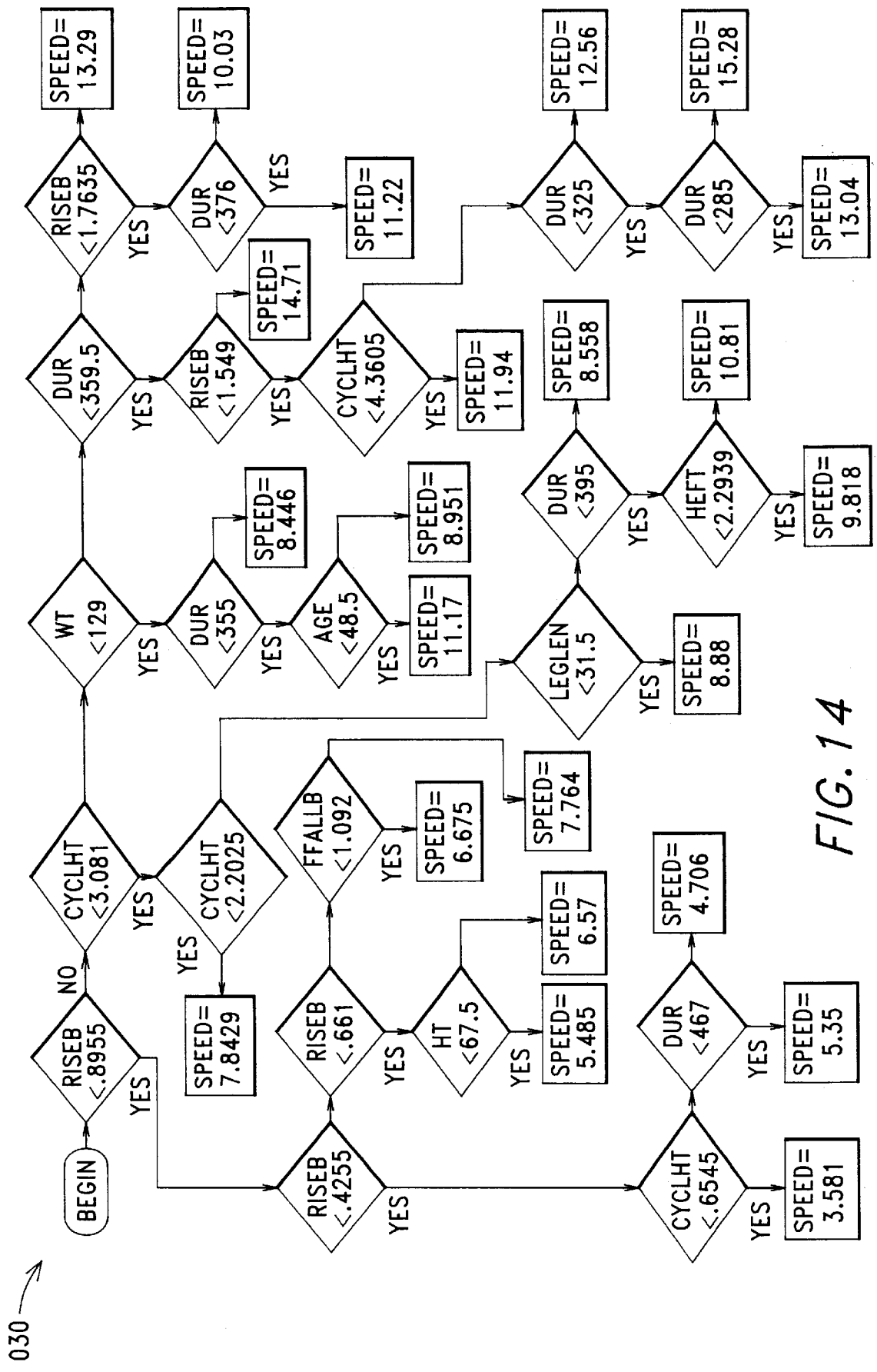
FIG. 14 is a flow chart illustrating one embodiment of a gait model used by the personal fitness monitoring device of FIG. 7.

FIG. 14 shows the algorithm for estimating locomotor speed in feet/sec as a result of the above step parameters and five personal data 005 items:

wt—the body weight in pounds;
age—the age in years;
ht—the body height in inches;
leglen—the length of the leg in inches from the lateral protrusion of the innominate or "hipbone" to the lateral malleolus of the ankle; and
heft—the wt/ht.

The procedure shown in FIG. 14 is the result of a regression tree analysis, which produces a discrete predicted value for each leaf of a tree of binary decisions based on predictor variables. The final locomotor speed used for a step is the average of its speed derived by the algorithm and the speed derived for the previous step. This averaging produces a smoothing effect. The model shown is based on 24 subjects from 15 to 72 years old, and produces an average error in predicted speed of less than one percent for those 24 subjects and also for 8 others whose data were not used in the model. Some individuals had higher errors of prediction, which suggests that the model can be improved by re-running the regression tree analysis with more data on more subjects who vary on the various predictor variables. Other embodiments of the invention could use such an improved model, or use other modeling techniques, such as neural networks or genetic search algorithms to derive improved models.

Returning to FIG. 12 and having calculated the step's gait, duration, and speed, the monitor sensors process 154 puts in the step queue those items, the time of the step's starting footfall, and the heart rate 226 at the last heart beat 170 detected before the end of the step, as the step statistics 190 for the step. If the exercise session has already started, then the monitor sensors process 154 de-queues and reports to the track user status process 156 the step statistics 190 for any unreported steps, and similar data for any ongoing rest period. The collection and analysis cycle then begins again when a sample timer interrupt 194 occurs. If, however, the session has not begun, then the program checks to see if ten steps have been taken without an intervening rest, and, if so reports to the ear menu process 152 a 'locomotion starts' event, also shown in FIG. 11. If instead five minutes have passed without any steps then a 'long pause' state is added to the state queue 191, as also shown in FIG. 11, and processed by the state/menu loop 192. This leads to the LONG PAUSE IN LOCOMOTION row of dialogue in Table 1.

Track User Status Process 156 Details. For each step whose step statistics 190 are reported to it, this process accumulates distance traveled,
duration of the session,
average of heart rate 226,
average of exercise effort level in METs, and
total energy expended in kilocalories.

These are passed as session status 178 to the ear menu process 152 whenever it needs to make an immediate report 204. The session status 178 is also passed to the summarize session process 158 at the end of the session. The track user status process 156 also monitors for "alarm" conditions and reports any triggering conditions whenever the user has already requested that a particular alarm be set. It reports a milepost alarm trigger 176 when the user's distance traveled has reached another chosen increment, such as ¼ mile. It reports a heart alarm trigger 176 whenever the user's heart rate 226 goes consistently into or consistently out of the chosen band. Analogously it reports a cruise control alarm trigger 176 whenever the user's locomotor speed goes consistently into or consistently out of the chosen speed band.

Energy and effort are calculated for each step first by estimating $VO_2$—the ml of Oxygen consumed per minute for each kilogram of body weight. $VO_2$ is estimated from locomotor velocity, V, in meters per minute, by two formulas, one for walking:

$$VO_2 = 0.177\, V - 1.866$$

and another for running:

$$VO_2 = 0.177 V + 2.989.$$

Intensity of exercise effort, in units of metabolic equivalents, called METs, is derived from $VO_2$, by a simple equivalence relation:

$$1\ \text{Met} = 3.5\ (VO_2)$$

Kilocalories burned, an energy measure, is determined as 5 kilocalories for each liter of Oxygen consumed, determined in turn by integrating $VO_2$ times the user's body weight.

To facilitate the subsequent computing of fitness while saving memory space, the track user status process 156 accumulates some summations over all locomotor steps:

the number of steps,
the sum of heart rate 226,
the sum of squared heart rate,
the sum of $VO_2$,
the sum of squared $VO_2$, and
the sum of cross products of $VO_2$ and heart rate 226.

These are passed to the summarize session process 158 as the step summations 180.

Summarize Session Process 158 Details. This process receives session status 178 and step summations 180 from the track user status process 156, and uses these to create the session summary 184. The latter consists of:

duration of the session
total kilocalories burned
distance traveled
raw fitness 232
average of heart rate 226
slope of EE versus heart rate 226
intercept of EE versus heart rate 226

Figure 17:
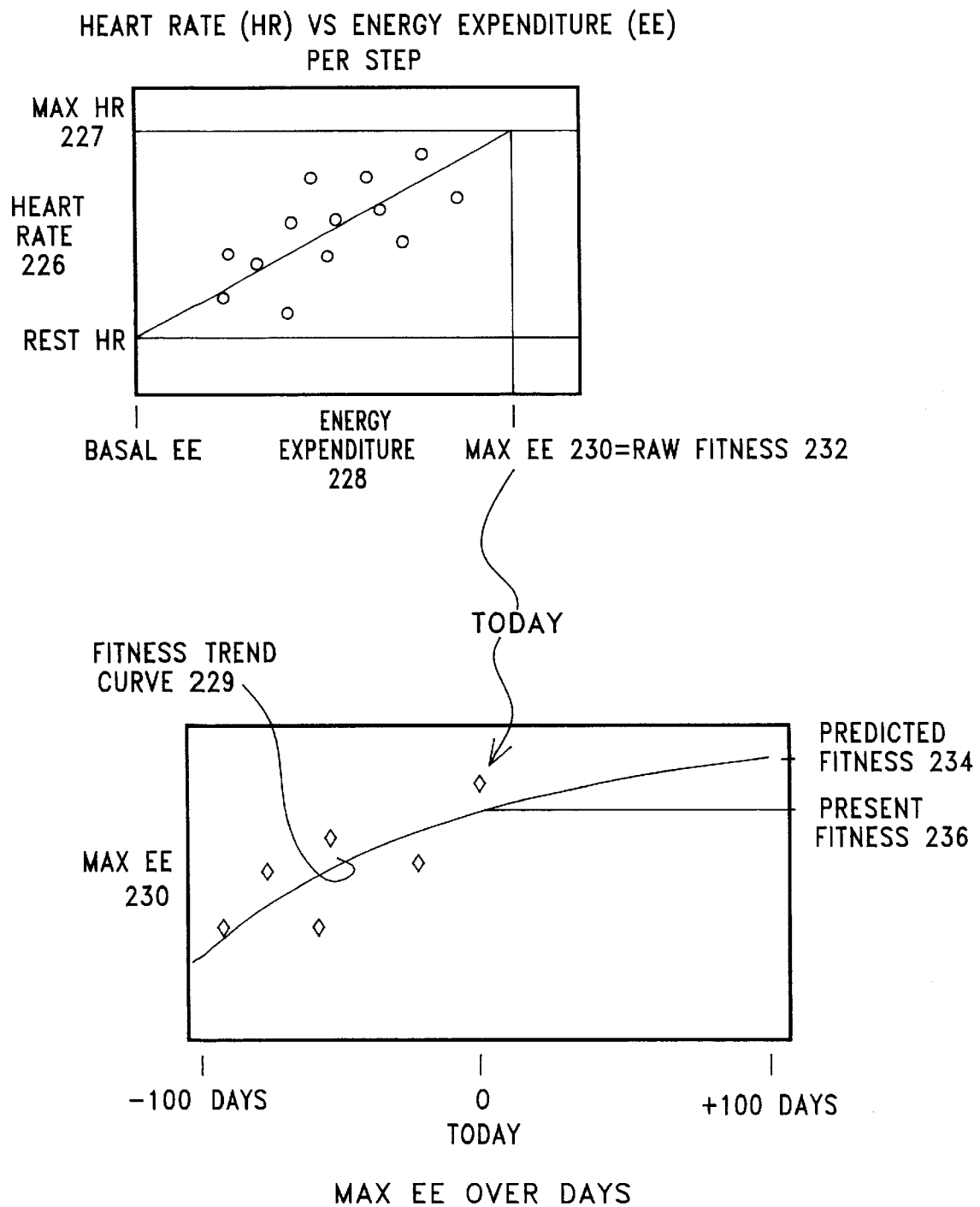
FIG. 17 is a diagrammatic illustration of one embodiment of how the personal fitness monitoring device of FIG. 7 computes a fitness trend.

FIG. 17 shows graphically how raw fitness 232 is computed. The user's maximum heart rate, max HR 227, is estimated from age in years for females by max HR=209−(0.7 Age)

and for males by:

max HR=212−(0.8 Age)

The system uses the step summations 180 to perform a least-squares linear regression on a set of data points, one for each locomotor step, where y is the energy expenditure 228 during a step and x is the heart rate 226 during the step. The upper half of FIG. 17 shows how the regression line is extended to intersect the projection of max HR 227, so that the projection from that intersection to the x axis gives the maximum aerobic energy expenditure, max EE 230. This maximum is our raw fitness 232 score for the exercise session. This technique of estimating max EE 230—by projecting energy expenditure 228 to intercept max HR 227—is standard in exercise physiology textbooks. The advantage of the present invention is that it allows us to have many more data points than any previous test based on this estimation procedure. This advantage in turn depends on being able to estimate locomotor speed and gait—whether walking or running—for each step. The method for doing so is described under the "Monitor Sensors Process Details" section. The slope and intercept of the linear regression are stored in the session summary 184 for later use to see if the user's heart rate 226 is in reasonable agreement with energy expenditure 228.

This method for computing raw fitness is not a requirement of the invention, but serves to illustrate the basic principle. Refinements upon this principle may be employed, including the introduction of a suitable time lag or shift between the expended energy and associated heart rate series. Such a shift may be introduced in order to more accurately account for the physiological lag in heart rate in response to changes in expended energy. The suitable lag may be found empirically by iteratively testing successively longer lags until the unexplained variance in the resulting correlation of heart rate and expended energy is minimized. However, any suitable statistical method that accounts for heart rate lag may be employed.

Summarize Day Process 160 Details. This process uses the session summaries 184 from one or more sessions in a day to create day summary 186. A day summary 186 can be done after any session in a day. The final day summary 186 for a day is done only when that day is known to be past. When a day summary 186 is done the most recent day's the session summary 184 records are deleted from the database. A day summary 186 consists of:
total duration of the day's sessions
total kilocalories burned
total distance traveled
average of raw fitness 232
average of heart rate 226
average slope of energy expenditure 228 versus heart rate 226
average intercept of energy expenditure 228 versus heart rate 226
present fitness 236—the best estimate of current fitness
predicted fitness 234—the estimate of fitness 100 days in the future
fit_trend—the qualitative derivative of current fitness, whether increasing, level or decreasing
fit_zone—the qualitative fitness zone tritile_zone—qualitative fitness tritile subzone
days_to_tritile—the number of days until fitness is predicted to cross a fitness tritile border.

The first seven items are either summed or averaged over the day's sessions. The slope and intercept of energy expenditure 228 versus heart rate 226 are used to estimate what the user's heart rate should be, given a known current energy expenditure 228. This estimated rate is used in comparison with the actual heart rate 226 as measured by the heart beat subsystem 067 in order to detect any significant difference. Such a difference would be diagnostic of violations in the assumptions under which expended energy is computed, such as the existence of a grade in the terrain the user is locomoting or other anticipated condition. A persistent violation could be reported to the user as a problem in need of technical support.

The last six items in the day summary 186 derive from a fitness trend computation, done after each day of use. All six items together are called the fitness prediction 081.

FIG. 17 shows graphically how fitness trend is computed by a curve-fitting procedure, producing a fitness trend curve 229. The data points have as their y-value the average raw fitness 232 estimates from the day summaries 186 of up to 100 previous days of use, and their x-value is ordinal date. The system uses an iterative process to minimize the least-squares fit of a decaying exponential to these data. More recent data is given more weight in the curve fitting by doubling the presence of each recent data point. The system fits the following model:

$$y = A + (\text{sign}) * Exp(a + k*t), \text{ where } -100 < t < 100,$$

where A is a constant representing the value of convergence of a decaying exponential, where (sign) indicates whether the curve is growing or decaying, where a and k are curve fitting parameters describing the shape of the exponential, and where t, in days, ranges from −100 to 100, with t=0 representing the current day.

The fitted fitness trend curve 229 will normally be a decaying exponential and either rise and begin to level off or fall and begin to level off. At times, the best fit will be a growing exponential, and in this case, the curve fitting algorithm is replaced with a linear regression.

The set of possible y-values are divided into seven zones, the values of fit_zone mentioned above, corresponding to qualitative levels of fitness. These zones are labeled: Excellent, Good, Above Average, Average, Below Average, Poor, and Very Poor. The y-value dividing points between these zones are adjusted dynamically, based on the user's gender and age using stored data reflecting norms for relative maximal oxygen consumption for men and women developed by the YMCA, adopted from Golding et al. (1986), *The Y's Way to Physical Fitness*, 3d ed.

The fitness prediction 081 derived from the curve fitting process are used in a report, shown in Table 2 as the fitness trend report 212. This report is constructed for presentation to the user upon demand through the ear menu process 152. The fitness trend report 212 has six variable fields which are filled in based on the fitness prediction 081:
the name of the qualitative fitness zone of the user's present fitness 236,
which step of 3 within that zone present fitness 236 lies,
whether the fitness trend is falling, rising, or holding steady,
what the next adjacent step would be,
the qualitative period of time within which it is projected that that transition will take place, and
the numeric value of present fitness 236 in METs.

If the user has not used the fitness monitor 001 for more than 5 days, then a fitness trend report 212 is not given, and the user is told, "I don't have an estimate for when you'll graduate to the next fitness category, you haven't used me recently. It's been over five days." The purpose of this message is to avoid making fitness estimates and projections without suitably current data.

The qualitative period of time for future transitions is constructed as follows. If the projected time in days to the next transition, days_to_tritile, is less than 4 days, the user is told the transition will occur "in the next few days." If the span of days is between 4 and 11 days, the user is told, "in the next week or so." For 11 to 26 days, "in a few weeks" is used. For 26 to 41 days, "in a month or so" is used. For 41 to 76 days, "in a couple of months" is used. Finally, for over 76 days, "in three months or so" is used.

The fitness trend report 212 is constructed in such a way that hysteresis effect is applied to fitness levels and transition times. An overlap in values is established between adjacent levels of fitness or time. It is required that the user's present fitness 236 or days_to_tritile exceed the value at the boundary between fitness steps or qualitative times by a certain amount, delta, before a new qualitative category for fitness or time is established. In ascending from one category to another, this delta is added to the boundary to form the threshold of making the qualitative change. In descending from one category to another, this delta is subtracted from the boundary to form the threshold for making the qualitative change.

For example, if delta is 1.0 and the boundary is between "Good" and "Excellent" is at 12.0 METs, then when ascending, a fitness would be classified as "Good" until its value exceeds 13.0, at which point it would be judged as "Excellent." When descending, the "Excellent" category would pertain until the value reached 11.0, at which point it would be judged as "Good."

The deltas for present fitness 236 and days_to_tritile are computed based on the proportionate size of the category into which falls the present value. For example, the delta associated with "in a month or so" is larger than the delta associated with "in the next few days."

This technique for smoothing the transition between qualitative categories has the advantage of avoiding a "whipsaw" effect on the user due to minor and insignificant changes in the values reported when those changes are occurring near a boundary between qualitative categories. Depending on the proper sizing of delta, changes between qualitative category are not reported until the changes are substantive and meaningful. This allows us to accentuate these transitions with positive reinforcement to the user in the way of congratulatory messages presented when a transition between qualitative categories occurs. For example, when the user transits from "a month or so" to "a few weeks", this message is presented, "Congratulations! Your new fitness step is getting closer!"

Because it is necessary to compare the user's current status and most recent past status in order to make the judgment as to whether a boundary has been crossed in qualitative terms, the following variables are stored in the user database 166 as part of the day summary 186, reflecting the most recent prior day's qualitative values: fitness step, days to transition, and whether congratulatory messages were issued for either type of transition.

Make Long-term Summary Process 162 Details. This module uses the day summary 186 records in the user database 166 to summarize various periods of time used in reports 172. Time spans include the previous day, the current calendar week since the previous Sunday, the calendar week prior to the previous one, and the calendar month prior to the current one.

Although many specific examples of various embodiments of the present invention have been described in detail above, these examples are to be considered as illustrative and not restrictive. Therefore, the invention is not to be limited to the details given herein, but may be modified within the scope of the appended claims.

What is claimed is:

1. A personal aerobic fitness monitoring device for assessing the aerobic fitness of an individual as the individual exercises, the aerobic fitness monitoring device comprising:

a pedometer for determining and outputting data representing the locomotion of the individual;

a heart rate monitor for determining and outputting data representing the heart rate of the individual; and determination means for calculating the aerobic fitness of the individual as the individual exercises, the determination means using personal data provided by the individual in combination with the data outputs of the pedometer and the heart rate monitor to calculate the aerobic fitness of the individual during the course of a normal workout without the use of the execution or conduct of a prescribed and particular fitness assessment protocol.

2. A personal aerobic fitness monitoring device according to claim 1 wherein the pedometer includes:

an accelerometer for measuring and outputting a plurality of data points representing a corresponding plurality of vertical accelerations caused by each step of an individual as the individual is walking or running; and determination means for calculating a variable distance traveled for each step taken by the individual, the determination means using personal data provided by the individual in combination with the plurality of data points representing a corresponding plurality of vertical accelerations caused by each step to calculate the variable distance traveled for each step taken by the individual.

3. A personal aerobic fitness monitoring device according to claim 2 wherein the pedometer further includes a clock to segment the output of the accelerometer into a time series of data points representing the output of the accelerometer.

4. A personal aerobic fitness monitoring device according to claim 1 wherein the device further includes a user interface for communicating with the user, the user interface including:

menus including a plurality of various user selectable options available to the user for controlling the operation of the personal aerobic fitness monitoring device;

means for successively presenting the various user selectable options of the menus to the user; and a single selecting mechanism controlled by the user for selecting a desired one of the various user selectable options of the menus, the user controlled selecting mechanism being arranged such that the user selects the desired option by actuating the single selecting mechanism during or immediately following the time during which the desired option is being presented.

5. A personal aerobic fitness monitor according to claim 4 wherein the means for successively presenting the various user selectable options is provided by audio producing means for presenting the user selectable options to the user in the form of recorded or synthesized speech.

6. A personal aerobic fitness monitoring device according to claim 5 wherein the device further includes an auxiliary audio fader arrangement, the audio fader arrangement including:

an auxiliary audio input connector for receiving an auxiliary audio input signal from an auxiliary audio device; and fader means controlled by the operation of the personal aerobic fitness monitoring device for connecting the auxiliary audio input signal to an audio output device used by the user interface of the personal aerobic fitness monitoring device to present the user interface messages, the fader means being configured to suppress the auxiliary audio input signal when the user interface of personal aerobic fitness monitoring device presents a message to the user.

7. A personal aerobic fitness monitoring device according to claim 1 wherein the device further includes a predicting arrangement for tracking and predicting the aerobic fitness of the individual, the predicting arrangement including:

memory means for storing the data representing the aerobic fitness of the individual each time the individual exercises using the personal aerobic fitness monitoring device; and aerobic fitness projecting means for calculating a projected aerobic fitness of the individual, the aerobic fitness projecting means using the stored data representing the aerobic fitness of the individual each time the individual exercises using the personal aerobic fitness monitoring device to calculate the projected aerobic fitness of the individual.

8. A personal aerobic fitness monitoring device according to claim 1 wherein the pedometer and the heart rate monitor are configured to determine and output a substantially continuous stream of synchronized and substantially simultaneously obtained pairs of data points representing both the locomotion and the heart rate of the individual during the course of a normal workout, and the determination means uses at least a portion of the continuous stream of synchronized and substantially simultaneously obtained pairs of data points obtained during the course of a normal workout to calculate the fitness of the individual.

9. A method of assessing the aerobic fitness of an individual as the individual exercises, the method comprising the steps of:

using a pedometer to determine and output data representing the locomotion of the individual;

using a heart rate monitor to determine and output data representing the heart rate of the individual; and calculating the aerobic fitness of the individual as the individual exercises using personal data provided by the individual in combination with the data outputs of the pedometer and the heart rate monitor during the course of a normal workout without the use of the execution or conduct of a prescribed and particular fitness assessment protocol.

10. A method according to claim 9 wherein the step of using a pedometer to determine and output data representing the locomotion of the individual includes the step of calculating a distanced traveled by the individual as the individual is walking or running, the step of calculating a distance traveled including the steps of:

using an accelerometer to measure and output a plurality of data points representing a corresponding plurality of vertical accelerations caused by each step of the individual as the individual is walking or running; and calculating a variable distance traveled for each step taken by the individual using personal data provided by the individual in combination with the plurality of data points representing a corresponding plurality of vertical accelerations caused by each step taken by the individual.

11. A method according to claim 10 wherein the step using an accelerometer to measure and output a plurality of data points representing a corresponding plurality of vertical accelerations caused by each step of the individual as the individual is walking or running includes the step of using a clock to segment the output of the accelerometer into a time series of data points representing the output of the accelerometer.

12. A method according to claim 9 wherein a personal aerobic fitness monitor device is used to perform the step of calculating the aerobic fitness of the individual, the personal aerobic fitness monitor including a user interface for communicating with the user.

13. A method according to claim 12 wherein the method further includes the steps of:

using predetermined menus to provide a plurality of various user selectable options for controlling the operation of the personal aerobic fitness monitoring device by presenting the various user selectable options of the menus to the user;

using a single selecting mechanism to select a desired one of the various user selectable options of the menus by actuating the single selecting mechanism during or immediately following the time during which the desired option is being presented.

14. A method according to claim 13 wherein the step of presenting the various user selectable options to the user includes the step of presenting the options to the user in the form of recorded or synthesized speech.

15. A method according to claim 14 wherein the method further includes steps of:

receiving an auxiliary audio input signal from an auxiliary audio device;

connecting the auxiliary audio input signal to an audio output device used by the user interface of the personal aerobic fitness monitoring device to present the user interface messages, and when the user interface of personal aerobic fitness monitoring device presents a message to the user, suppressing the auxiliary audio input signal.

16. A method according to claim 12 wherein the method further includes the steps of:

using a memory storage mechanism of the device to store the data representing the aerobic fitness of the individual each time the individual exercises using the personal aerobic fitness monitoring device; and using a aerobic fitness projecting arrangement to calculate a projected aerobic fitness of the individual using the stored data representing the aerobic fitness of the individual each time the individual exercises using the personal aerobic fitness monitoring device to calculate the projected aerobic fitness of the individual.

17. A method according to claim 9 wherein the steps of determining and outputting data representing the locomotion of the individual and the heart rate of the individual include the step of determining and outputting a substantially continuous stream of synchronized and substantially simultaneously obtained pairs of data points representing both the locomotion and the heart rate of the individual during the course of a normal workout, and the step of calculating the fitness of the individual includes the step of using at least a portion of the continuous stream of synchronized and substantially simultaneously obtained pairs of data points obtained during the course of a normal workout to calculate the fitness of the individual.

18. A personal aerobic fitness monitoring device for assessing the aerobic fitness of an individual as the individual exercises, the aerobic fitness monitoring device comprising:

exertion determination means for determining and outputting data representing the exertion of the individual as the individual is exercising;

a heart rate monitor for determining and outputting data representing the heart rate of the individual; and determination means for calculating the aerobic fitness of the individual as the individual exercises, the determination means using personal data provided by the individual in combination with the data outputs of the exertion determination means and the heart rate monitor to calculate the aerobic fitness of the individual during the course of a normal workout without the use of the execution or conduct of a prescribed and particular fitness assessment protocol.

19. A personal aerobic fitness monitoring device according to claim 18 wherein the exertion determination means is an apparatus for determining the exertion of the individual as the individual rides a bicycle.

20. A personal aerobic fitness monitoring device according to claim 18 wherein the exertion determination means and the heart rate monitor are configured to determine and output a substantially continuous stream of synchronized and substantially simultaneously obtained pairs of data points representing both the exertion and the heart rate of the individual during the course of a normal workout, and the determination means uses at least a portion of the continuous stream of synchronized and substantially simultaneously obtained pairs of data points obtained during the course of a normal workout to calculate the fitness of the individual.

21. A method of assessing the aerobic fitness of an individual as the individual exercises, the method comprising the steps of:

determining and outputting data representing the exertion of the individual;

using a heart rate monitor, determining and outputting data representing the heart rate of the individual; and calculating the aerobic fitness of the individual as the individual exercises using personal data provided by the individual in combination with the data outputs representing the exertion of the individual and the heart rate of the individual during the course of a normal workout without the use of the execution or conduct of a prescribed and particular fitness assessment protocol.

22. A method according to claim 21 wherein the step of determining and outputting data representing the exertion of the individual includes the step of determining and outputting data representing the exertion of the individual as the individual rides a bicycle.

23. A method according to claim 21 wherein the steps of determining and outputting data representing the locomotion of the individual and the heart rate of the individual include the step of determining and outputting a substantially continuous stream of synchronized and substantially simultaneously obtained pairs of data points representing both the locomotion and the heart rate of the individual during the course of a normal workout, and the step of calculating the fitness of the individual includes the step of using at least a portion of the continuous stream of synchronized and substantially simultaneously obtained pairs of data points obtained during the course of a normal workout to calculate the fitness of the individual.

* * * * *